(12) United States Patent
Ding et al.

(10) Patent No.: US 6,838,558 B2
(45) Date of Patent: Jan. 4, 2005

(54) PYRAZOLOBENZODIAZEPINES

(75) Inventors: Qingjie Ding, Clifton, NJ (US); Jin-Jun Liu, Warren Township, Somerset County, NJ (US); Giacomo Pizzolato, Glen Ridge, NJ (US); Chung-Chen Wei, Foster City, CA (US); Peter Michael Wovkulich, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 33 days.

(21) Appl. No.: 10/122,559

(22) Filed: Apr. 15, 2002

(65) Prior Publication Data

US 2002/0183514 A1 Dec. 5, 2002

Related U.S. Application Data

(62) Division of application No. 09/548,091, filed on Apr. 12, 2000, now Pat. No. 6,440,959.
(60) Provisional application No. 60/130,370, filed on Apr. 21, 1999.

(51) Int. Cl.[7] .................. C07D 243/18; C07D 243/10
(52) U.S. Cl. ............................. 540/505; 540/557
(58) Field of Search ..................... 540/505, 557

(56) References Cited

FOREIGN PATENT DOCUMENTS

| EP | 0 988 863 | 3/2000 |
|---|---|---|
| WO | WO 98/14450 | 4/1998 |

OTHER PUBLICATIONS

M. A. Berghot, Arch. Pharm. 325: 285–289 (1992).
Chemical Abstracts, vol. 117, No. 7, Aug. 17, 1992.
D. W. Zaharevitz, et al., Cancer Research, US, American Association for Cancer Research, Baltimore, MD vol. 59, No. 59, Jun. 1, 1999, pp. 2566–2569, XP002118393.

*Primary Examiner*—Brenda Coleman
(74) *Attorney, Agent, or Firm*—George W. Johnston; Patricia S. Rocha-Tramaloni

(57) ABSTRACT

Disclosed are novel pyrazolobenzodiazepines having the formula

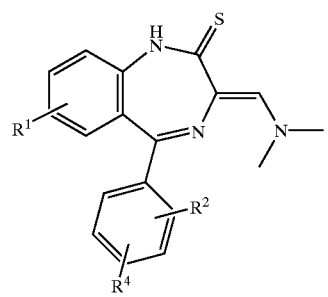

and

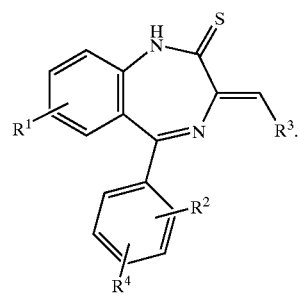

These compounds are useful in the preparation of the pyrazolobenzodiazepines of formula I, which are useful in the treatment and control of solid tumors.

26 Claims, No Drawings

PYRAZOLOBENZODIAZEPINES

This application is a Divisional application of Ser. No. 09/548,091, filed Apr. 12, 2000 now U.S. Pat. No. 6,440,959, which claims priority of Provisional application Serial No. 60/130,370, filed Apr. 21, 1999.

FIELD OF THE INVENTION

The present invention is directed to novel pyrazolobenzodiazepines which inhibit cyclin-dependent kinases (CDKs), in particular CDK2. These compounds and their pharmaceutically acceptable salts, and prodrugs of said compounds, are anti-proliferative agents useful in the treatment or control of cell proliferative disorders, in particular cancer. The invention is also directed to pharmaceutical compositions containing such compounds, and to methods for the treatment and/or prevention of cancer, particularly in the treatment or control of solid tumors. The compounds of the invention are especially useful in the treatment or control of breast, colon, lung and prostate tumors. The invention is also directed to intermediates useful in the preparation of the above anti-proliferative agents.

BACKGROUND OF THE INVENTION

Uncontrolled cell proliferation is the hallmark of cancer. Cancerous tumor cells typically have some form of damage to the genes that directly or indirectly regulate the cell-division cycle.

Cyclin-dependent kinases (CDKs) are enzymes which are critical to cell cycle control. See, e.g., Coleman et al., "Chemical Inhibitors of Cyclin-dependent Kinases," *Annual Reports in Medicinal Chemistry*, vol. 32, 1997, pp. 171–179. These enzymes regulate the transitions between the different phases of the cell cycle, such as the progression from the $G_1$ phase to the S phase (the period of active DNA synthesis), or the progression from the $G_2$ phase to the M phase, in which active mitosis and cell-division occurs. See, e.g., the articles on this subject appearing in *Science*, vol. 274, Dec. 6, 1996, pp 1643–1677.

CDKs are composed of a catalytic CDK subunit and a regulatory cyclin subunit. The cyclin subunit is the key regulator of CDK activity, with each CDK interacting with a specific subset of cyclins: e.g. cyclin A (CDK1, CDK 2). The different kinase/cyclin pairs regulate progression through specific stages of the cell cycle. See, e.g., Coleman, supra.

Aberrations in the cell cycle control system have been implicated in the uncontrolled growth of cancerous cells. See, e.g., Kamb, "Cell-Cycle Regulators and Cancer," *Trends in Genetics*, vol. 11, 1995, pp.136–140; and Coleman, supra. In addition, changes in the expression of or in the genes encoding CDK's or their regulators have been observed in a number of tumors. See, e.g., Webster, "The Therapeutic Potential of Targeting the Cell Cycle," *Exp. Opin. Invest. Drugs*, Vol. 7, pp. 865–887 (1998), and references cited therein. Thus, there is an extensive body of literature validating the use of compounds inhibiting CDKs as anti-proliferative therapeutic agents. See, e.g. U.S. Pat. No. 5,621,082 to Xiong et al; EP 0 666 270 A2; WO 97/16447; and the references cited in Coleman, supra, in particular reference no. 10. Thus, it is desirable to identify chemical inhibitors of CDK kinase activity.

It is particularly desirable to identify small molecule compounds that may be readily synthesized and are effective in inhibiting one or more CDKs or CDK/cyclin complexes, for treating one or more types of tumors.

Several classes of compounds that inhibit cyclin-dependent kinases have been and are being investigated as therapeutic agents. These are, for example, as follows:

Analogs of Flavopiridol:
U.S. Pat. No. 5,733,920 (Mitotix)
WO 98/1344 (Bristol-Myers Squibb)
WO 97/42949 (Bristol-Meyers Squibb)
Purine Derivatives:
WO 98/05335 (CV Therapeutics)
WO 97/20842 (CNRS)
Acridones and Benzothiadiazines:
WO 98/49146 A2 (US Dept. of Health and Human Services)
Antisense
U.S. Pat. No. 5,821,234 (Stanford University).

Furthermore, certain N,N-substituted dihydropyrazolobenzodiazepines have been disclosed in an article discussing CNS-acting compounds. See, M. A. Berghot, *Arch. Pharm.* 325:285–289 (1992).

There continues to be a need for easily synthesized, small molecule compounds for the treatment of one or more types of tumors, in particular through regulation of CDKs. It is thus an object of this invention to provide such compounds and compositions containing such compounds.

SUMMARY OF THE INVENTION

The present invention relates to pyrazolobenzodiazepines capable of inhibiting the activity of one or more CDKs, in particular CDK2. Such compounds are useful for the treatment of cancer, in particular solid tumors. In particular the compounds of the present invention are especially useful in the treatment or control of breast, colon, lung and prostate tumors. The invention is also directed to intermediate compounds useful in the preparation of the above-mentioned pyrazolobenzodiazepines.

The compounds of the present invention are compounds of formula I below

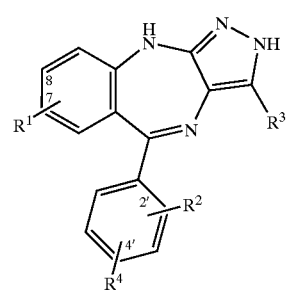

I and prodrugs and metabolites of the foregoing compounds, as well as pharmaceutically acceptable salts of each of the foregoing compounds, wherein $R^1$ is selected from the group consisting of
—H,
—$NO_2$,
—CN,
-halogen,
-lower alkyl which is straight-chained and which optionally may be substituted by the group consisting of —OH and halogen,
—$OR^5$,
—$R^6OR^7$,
$COOR^7$,
$CONR^8R^9$ (a.k.a. carboxamide), $NR^{10}R^{11}$,
—$NHCOR^{12}$, and
—$NHSO_2R^{13}$;

$R^2$ and $R^4$ are each independently selected from the group consisting of
—H,
halogen,
—$NO_2$,
—$CF_3$, and
-straight chained lower alkyl;

$R^3$ is selected from the group consisting of
—H,
-lower alkyl which optionally may be substituted by
  —OH,
  —$OR^9$, F, and aryl,
-cycloalkyl,
-aryl,
heterocycle,
heteroaryl,
$COOR^7$
—CN,
-alkenyl,
—$CONR^8R^9$, and
-alkynyl;

$R^5$ is selected from lower alkyl which optionally may be substituted by halogen;

$R^6$ is selected from lower alkyl;

$R^7$ is selected from the group consisting of —H and lower alkyl;

$R^8$ and $R^9$ are each independently selected from the group consisting of —H and -lower alkyl which itself optionally may be substituted by —OH and —$NH_2$; alternatively, $R^8$ and $R^9$ may form a 5- or 6-membered heterocycle which optionally may be substituted by the group consisting of —OH, —$NH_2$, and lower alkyl;

$R^{10}$, $R^{11}$ and $R^{12}$ are each independently selected from the group consisting of —H and lower alkyl;

$R^{13}$ is selected from the group consisting of lower alkyl which optionally may be substituted by the group consisting of halogen and —$NR^{14}R^{15}$; and $R^{14}$ and $R^{15}$ are each independently selected from the group consisting of —H and lower alkyl which optionally may be substituted Halogen, or alternatively, —$NR^{14}R^{15}$ is a heterocycle.

The present invention is further directed to pharmaceutical compositions comprising a pharmaceutically effective amount of any one or more of the above-described compounds, or a pharmaceutically acceptable salt or prodrug thereof, and a pharmaceutically acceptable carrier or excipient.

The present invention is also directed to a method for treating solid tumors, in particular breast, colon, lung and prostate tumors, more specifically breast and colon tumors, by administering to a human patient in need of such therapy an effective amount of a compound of formula 1, its salts or prodrugs.

DETAILED DESCRIPTION OF THE INVENTION

As used herein, the following terms shall have the following definitions.

"Aryl" means an aromatic group having 5 to 10 atoms and consisting of 1 or 2 rings. Examples of aryl groups include phenyl and 1- or 2-naphthyl.

"Alkenyl" means a straight-chain or branched, substituted or unsubstituted, aliphatic unsaturated hydrocarbon having 2 to 6, preferably 2 to 4, carbon atoms and containing double bonds. Typical alkenyl groups include ethylene, propylene, isopropylene, butylene and the like. Preferred alkenyl groups are straight-chained.

"Alkynyl" means a straight-chain or branched, substituted or unsubstituted, aliphatic unsaturated hydrocarbon having 2 to 6, preferably 2 to 4, carbon atoms and containing triple bonds. Typical alkynyl groups include acetylene and the like. Preferred alkynyl groups are straight-chained.

"Cycloalkyl" means a non-aromatic, partially or completely saturated cyclic aliphatic hydrocarbon group containing 3 to 8 atoms. Examples of cycloalkyl groups include cyclopropyl, cyclobutyl, cyclopentyl and cyclohexyl.

"Effective Amount" means an amount of at least one compound of Formula I, or a pharmaceutically acceptable salt, prodrug or metabolite thereof, that significantly inhibits proliferation of a tumor cell, including human tumor cell lines.

"Halogen" means fluorine, chlorine, bromine or iodine. Preferred halogens are fluorine and chlorine.

"Heteroaryl" groups are aromatic groups having 5 to 10 atoms, one or 2 rings, and containing one or more hetero atoms. Examples of heteroaryl groups are 2-, 3- or 4-pyridyl, tetrazolyl, oxadiazolyl, pyrazinyl, quinolyl, pyrrolyl, and imidazolyl.

"Hetero atom" means an atom selected from N, O and S.

"Heterocycle" means a 3- to 10-membered non-aromatic, partially or completely saturated hydrocarbon group, such as tetrahydroquinolyl, which contains one or two rings and at least one hetero atom.

"$IC_{50}$" refers to the concentration of a particular pyrazolobenzodiazepine required to inhibit 50% of a specific measured activity. $IC_{50}$ can be measured, inter alia, as is described in Example 4, infra.

"Lower Alkyl" denotes a straight-chain or branched, substituted or unsubstituted, saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Pharmaceutically acceptable salt" refers to conventional acid-addition salts or base-addition salts which retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide.

"Pharmaceutically acceptable," such as pharmaceutically acceptable carrier, excipient, prodrug, etc., means pharmacologically acceptable and substantially non-toxic to the subject to which the particular compound is administered.

"Pharmaceutically active metabolite" means a metabolic product of a compound of formula I which is pharmaceutically acceptable and effective.

"Prodrug" refers to a compound that may be converted under physiological conditions or by solvolysis to any of the compounds of formula I or to a pharmaceutically acceptable salt of a compound of formula I. A prodrug may be inactive when administered to a subject but is converted in vivo to an active compound of formula I.

"Substituted," as in substituted alkyl, means that the substitution can occur at one or more positions and, unless otherwise indicated, that the substituents at each substitution site are independently selected from the specified options.

The Compounds

In one embodiment, the current invention is directed to compounds having the formula:

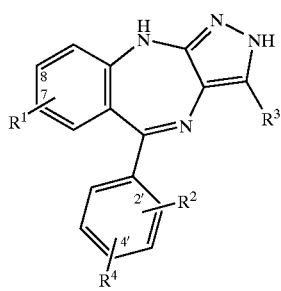

I and prodrugs and pharmaceutically active metabolites of compounds of formula I, and the pharmaceutically acceptable salts of the foregoing compounds, wherein $R^1$ through $R^{15}$ are as defined above.

In a preferred embodiment of the compounds of formula I, $R^1$ is on the 7 or 8 position and is selected from the group consisting of —H, —NO$_2$, —CN, —Halogen and unsubstituted lower alkyl. Preferred lower alkyls are methyl and ethyl.

In another preferred embodiment of the compounds of formula I, $R^2$ is on the 2' position and is selected from the group consisting of —H and —Halogen.

In another preferred embodiment of the compounds of formula I, $R^3$ is selected from the group consisting of unsubstituted lower alkyl, cycloalkyl, heterocycle, and heteroaryl. Preferred lower alkyl groups are methyl and ethyl. Preferred cycloalkyl groups are unsubstituted $C_3$–$C_5$.

In another preferred embodiment of the compounds of formula I, $R^4$ is at the 4' position and is selected from the group consisting of —H and —Halogen, most preferably $R^4$ is H.

In another preferred embodiment of the compounds of formula I, $R^5$ and $R^6$ are independently selected from methyl or ethyl, each of which optionally may be substituted by halogen. More preferably, $R^5$ is trifluoromethyl.

In another preferred embodiment of the compounds of formula I, $R^7$ is selected from the group consisting of —H, methyl and ethyl.

In another preferred embodiment of the compounds of formula I, $R^8$ and $R^9$ are each independently selected from —H, methyl, ethyl and hydroxyethyl. When $R^8$ and $R^9$ form a heterocycle, preferred heterocycle groups are 6-membered, unsubstituted, groups that most preferably include two heteroatoms. Most preferred heteroatoms are selected from O and N.

In another preferred embodiment of the compounds of formula I, $R^{10}$, $R^{11}$, and $R^{12}$ are each independently selected from the group consisting of —H, methyl and ethyl.

In another preferred embodiment of the compounds of formula I, $R^{13}$ is lower alkyl which optionally may be substituted by halogen, most preferably $R^{13}$ is methyl, ethyl, or trifluoromethyl.

In another preferred embodiment of the compounds of formula I, $R^{14}$ and $R^{15}$ are each independently selected from H, methyl, ethyl and heterocycle. Preferred heterocycles are 3–7 membered rings that include at least one Nitrogen.

The following intermediates are also examples of additional preferred compounds according to the present invention:

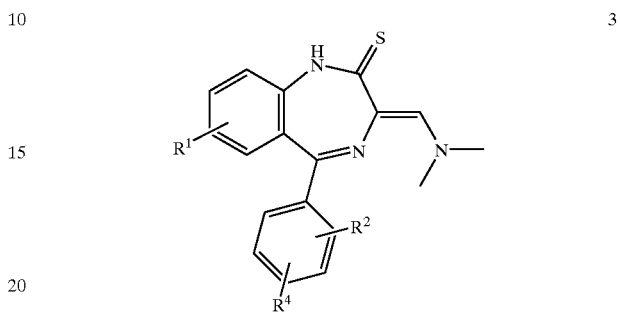

3 wherein $R^1$, $R^2$ and $R^4$ are as defined above;

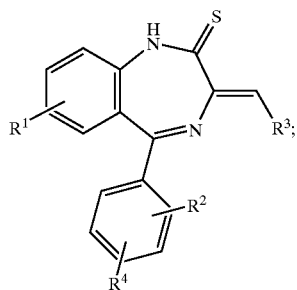

5

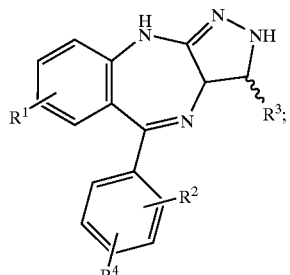

6 and

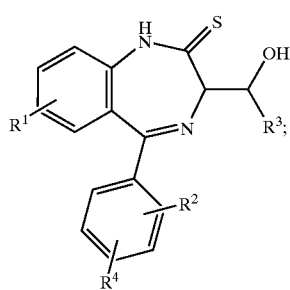

8 wherein, in each of the immediately foregoing formulas, each of $R^1$, $R^2$, $R^3$ and $R^4$ are as previously defined herein. These intermediates are useful in the synthesis of compounds of formula I.

The compounds disclosed herein and covered by the above formulae may exhibit tautomerism or structural isomerism. It is intended that the invention encompasses any tautomeric or structural isomeric form of these compounds, or mixtures of such forms, and is not limited to any one tautomeric or structural isomeric form utilized within the formulae drawn above.

Synthesis of Compounds of Formula I

The compounds of the invention may be prepared by processes known in the art. Suitable processes for synthesizing these compounds are provided in the examples. Generally, these compounds may be prepared according to the synthesis schemes provided below.

Compound 1 is either available from commercial sources or is synthesized by methods known in the art.

Scheme 1

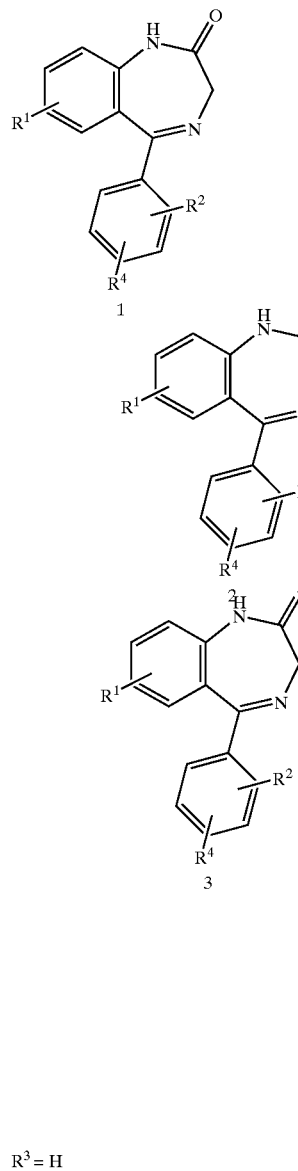

$R^3 = H$ a) Lawesson's reagent (a known reaction for most substitutions)
b) reaction with $Me_2N$—$CH(OEt)_2$
c) reaction with hydrazine.

Scheme 2

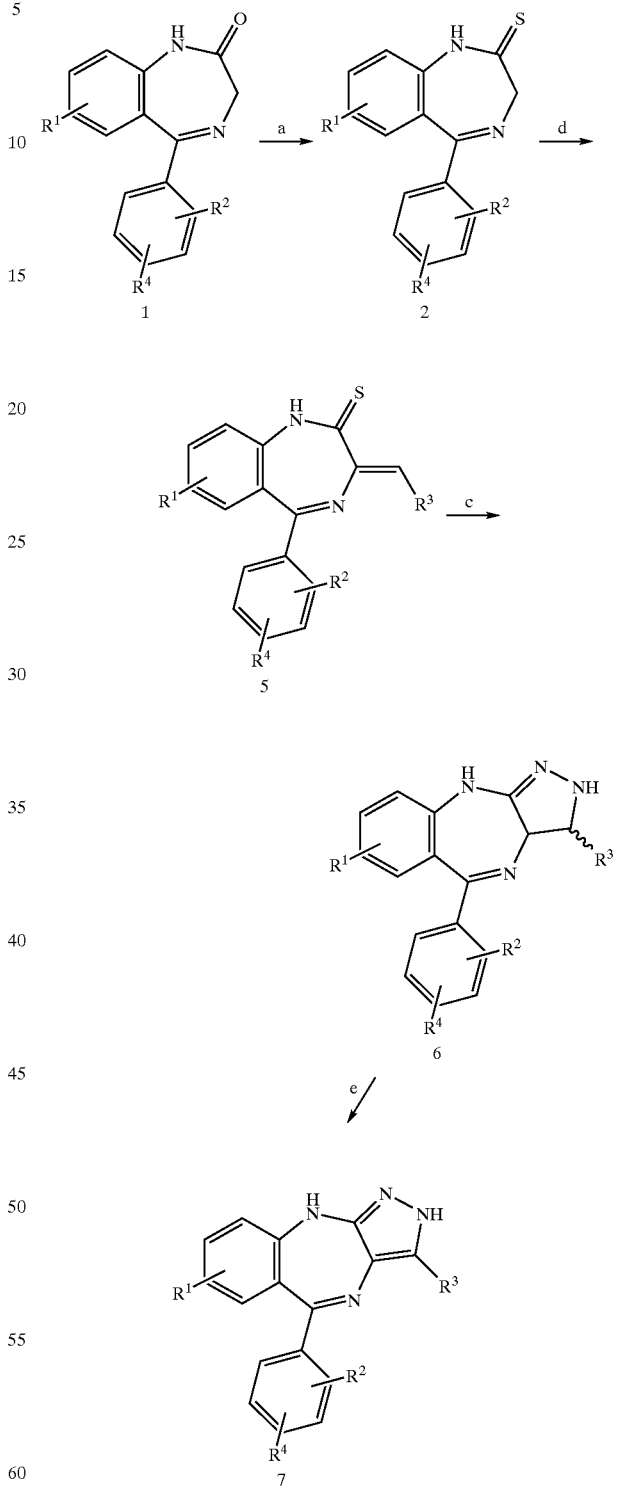

$R^3$ is other than H a) Lawesson's reagent (a known reaction for most substitutions)
d) reaction with $R^3$—CHO, in the presence of a base preferably piperdine
c) reaction with hydrazine
e) oxidation of dihydropyrazole to pyrazole (use of air in DMSO RT-150° C., or in the presence of air and base ($Cs_2CO_3$/DMF)).

Scheme 3
Alternative Scheme when R³ is other than H

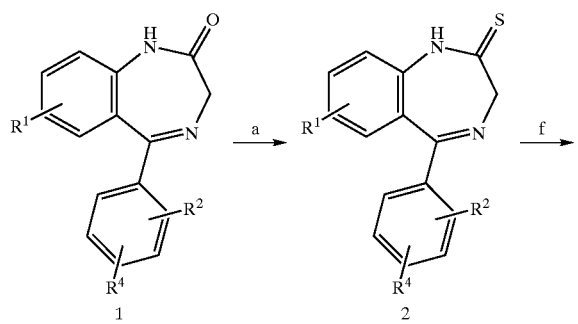

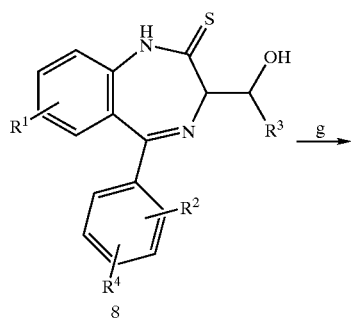

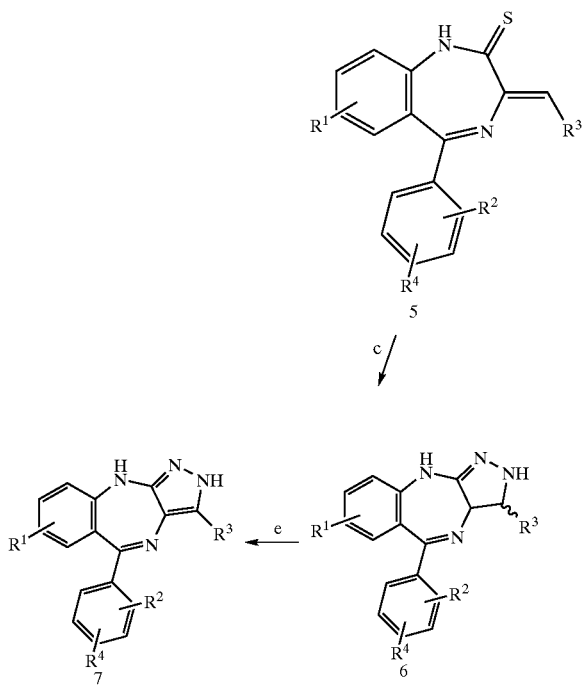

a) Lawesson's reagent (a known reaction for most substitutions)
f) reaction with R³—CHO, in the presence of a base preferably diazabicycloundecane or 2,2,6,6-tetramethylpiperidine.
g) dehydration, by treatment with weak acid (pyridinium p-toluenesulfonate, pyridinium acetate etc.) or with chlorotrimethylsilane in pyridine at reflux
c) reaction with hydrazine
e) oxidation of dihydropyrazole to pyrazole (use of air in DMSO RT-150° C., or in the presence of air and base ($Cs_2CO_3$/DMF).

Scheme 4
Transformation of R¹ or R² Functional Groups

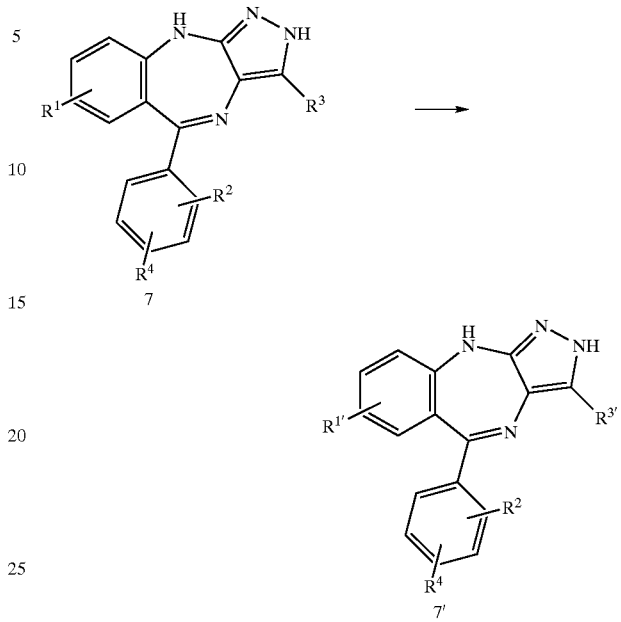

wherein $R^{1'}$ can be any of the options for $R^1$ as defined above and, similarly, $R^{3'}$ can be any of the options for $R^3$ as defined above.

Several substitutions may be obtained by chemical modification of existing functional groups using known methods as is exemplified in scheme 4 above. For example, when the desired $R^1=NH_2$, this substitution may be obtained by reduction of the corresponding nitro group. Similarly, when the desired $R^1=NHR'$ (where $R'=-COR^{12}$, $-SO_2R^{13}$, or $-R^{10}R^{11}$), this substitution may be obtained by reaction of the corresponding $R^1=NH_2$ compound with an acid halide or anhydride. When the desired $R^1=CONRR''$ (where R=hydrogen or lower alkyl, and R''=lower alkyl), this substitution may be obtained by reaction of the corresponding compound where $R^1=I$, with carbon monoxide and a primary or secondary amine in the presence of a palladium catalyst.

In addition, if $R^3$ in the starting material is $CO_2Et$, standard chemical modification may be used to produce compounds having the following corresponding $R^3$ groups: $CH_2OH$ (reduction); CHO (partial reduction); $CH_2NMe_2$ (reductive amination of the aldehyde); $CH_2OMe$ (alkylation of the alcohol); $CH=CH_2$ (olefination of the aldehyde); CONRR'' (where R=H or lower alkyl and R''=H or lower alkyl, aminolysis with the corresponding amine HNRR'' where R=H or lower alkyl and R''=H or lower alkyl); CONHNHR (where R=H, lower alkyl or aryl) (hydrazinolysis—reaction with hydrazine); CN (dehydration of the amide $CONH_2$).

In the foregoing schemes, compound 1 is either commercially available, for example from Sigma, or can be readily synthesized by methods known in the art. Thus, compound 2 is prepared from the corresponding lactam (compound 1) by the procedure of Sternbach et al., J. Org. Chem. 29:231 (1964) or by reaction with Lawesson's reagent.

Compositions/Formulations

In an alternative embodiment, the present invention is directed to pharmaceutical compositions comprising at least one compound of formula I or a prodrug thereof, or a pharmaceutically acceptable salt of a compound of formula I or a prodrug of such compound.

These pharmaceutical compositions can be administered orally, for example, in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, prodrugs of such compounds, or the salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of formula I, prodrugs thereof, and their salts, and compositions containing these compounds are useful in the treatment or control of cell proliferative disorders, in particular oncological disorders. These compounds and formulations containing said compounds are particularly useful in the treatment or control of solid tumors, such as, for example, breast and colon tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound of formula I can vary within wide limits and will be adjusted to the individual requirements in each particular case. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

EXAMPLES

The compounds of the present invention may be synthesized according to known techniques, such as for example the general schemes provided above. The following examples illustrate preferred methods for synthesizing the compounds and formulations of the present invention.

In the following examples the NMR data is provided in ppm relative to tetramethylsilane, in the solvent and spectrometer frequency as indicated.

Example 1

Pyrazoles Prepared According to Scheme 1
Step a: Reaction of Lactam (Compound 1) with Lawesson's Reagent to Form Thiolactam (Compound 2):
1.1 Compound A1: $R^1$=H, $R^2$=, $R^4$=H To a solution of 5.085 g (20 mmol) of lactam 1 (where $R^1$=H, $R^2$=F, and $R^4$=H) in 50 mL of dimethoxyethane at 75° C. was added 8.9 g (22 mmol) of Lawesson's reagent (2,4-bis(4-methoxyphenyl)-1,3-dithia-2,4-diphosphetane-2,4-disulfide; Pedersen, B. S.; Scheibye, S.; Nilsson, N. H.; Lawesson, S. -O., Bull. Soc. Chim. Belg., 1978, 87:223.). The mixture was stirred for 30 minutes, cooled and then poured into 10% sodium bicarbonate solution (aq.). The aqueous mixture was extracted with methylene chloride, and the extracts washed with water, dried over anhydrous sodium sulfate, filtered and concentrated under reduced pressure. The residue was recrystallized from methylene chloride-methanol to give 4.0 g of Compound A1 (thiolactam 2).

$^1$H nmr: (DMSO-d6, 300 mHz) 12.56 (s, 1H, NH), 7.10–7.65 (m, 8H), 4.59 (s, 2H).
1.2 Compound A2: $R^1$=F, $R^2$=$R^4$=H Compound A2 was prepared in the same manner as described above for Compound A1. $^1$H nmr: (DMSO-d6, 300 mHz) 12.50 (s, 1H, NH), 7.37–7.56 (m, 7H), 7.06 (dd, J=3, 9 Hz, 1H), 4.60 (br s, 2H).
Step b: Reaction of Thiolactam 2 With DMF Acetal To Form Dimethylaminomethylene Derivative 3:
1.3 Compound A3: $R^1$=Cl, $R^2$=Cl, $R^4$=H A solution of 0.999 g (3.1 mmol) of thiolactam 2 ($R^1$=Cl, $R^2$=Cl, $R^4$=H), 10 mL of dry tetrahydrofuran and 10 mL of dimethylformamide diethyl acetal was stirred at room temperature for 2 hours. Volatiles were removed under reduced pressure leaving a red-orange solid residue. Crystallization from hexane-ethyl acetate gave 0.716 g of Compound A3 (derivative 3 where $R^1$=Cl, $R^2$=Cl, $R^4$=H), as a red solid, mp 196–198° C. $^1$H nmr: (DMSO-d6, 400 mHz) 10.21 (s, 1H), 7.84 (s, 1H), 7.43–7.56 (m, 4H), 7.32 (dd, J=3, 9 Hz, 1H), 7.00 (d, J=9 Hz, 1H), 6.60 (d, J=3 Hz,1H), 3.27 (s, 6H).
Step c: Conversion of Dimethylaminomethylene Derivative 3 to Pyrazole 4:
1.4 Compound A4: $R^1$=Cl, $R^2$=Cl, $R^3$=$R^4$=H
5-(2-chlorophenyl)-7-chloro-pyrazolo[3,4][1,4]benzodiazepine To a solution of 0.265 g (0.71 mmol) in 10 mL of dry methylene chloride was added ca. 39.8 microliters (1.27 mmole) of anhydrous hydrazine. The mixture was stirred under an argon atmosphere for 85 min., then taken up in methylene chloride and washed with water, dried over anhydrous sodium sulfate, filtered and concentrated under reduced pressure to give 0.219 g of Compound A4 (pyrazole 4 where $R^1$=Cl, $R^2$=Cl, $R^4$=H) as a tan solid. The analytical sample was filtered through a short bed of silica gel, eluting with ethyl acetate, and then recrystallized from ethyl acetate. mp>300° C.

$^1$H nmr: (DMSO-d6, 400 mHz) 12.07 (s, 1H, NH), 8.03 (s, 1H, NH), 7.58 (s, 1H), 7.4–7.5 (m, 4H), 7.17 (dd, J=2, 9 Hz, 1H), 6.79 (d, J=9 Hz, 1H), 6.25 (s, 1H).

The following pyrazoles (compound 4) were prepared in accordance with scheme 1 and as described in steps a-c above:

1.5 Compound A5: $R^1=NO_2$, $R^2=Cl$, $R^3=H$, $R^4=H$
5-(2-chlorophenyl)-7-nitro-pyrazolo[3,4][1,4]benzodiazepine
$^1$H nmr: (DMSO-d6, 300 mHz) 9.16 (s, 1H, NH), 7.90 (dd, J=2, 8 Hz, 1H), 7.4–7.6 (m, 5 H), 7.08 (d, J=2 Hz, 1 H), 6.75 (d, J=8 Hz, 1H).

1.6 Compound A6: $R^1=Cl$, $R^2=H$, $R^3=H$, $R^4=H$
5-phenyl-7-chloro-pyrazolo[3,4][1,4]benzodiazepine
$^1$H nmr: (DMSO-d6, 200 mHz) 7.97 (s, 1H, NH), 7.62 (s, 1H), 7.35–7.60 (m, 5H), 7.29 (dd, J=2, 9 Hz, 1H), 6.93 (d, J=9 Hz, 1H), 6.60 (d, J=2 Hz, 1H).

1.7 Compound A7: $R^1=Cl$, $R^2=F$, $R^3=H$, $R^4=H$
5-(2-fluorophenyl)-7-chloro-pyrazolo[3,4][1,4]benzodiazepine
$^1$H nmr: (DMSO-d6, 400 mHz) 12.10 (s, 1H, NH), 8.01 (s, 1H), 7.60 (s, 1H), 7.5 (m, 2H), 7.18–7.33 (m, 3H), 6.83 (d, J=8 Hz, 1H), 6.47 (s, 1H).

1.8 Compound A8: $R^1=Cl$, $R^2=Cl$, $R^3=H$, $R^4=Cl$
5-(2,4-dichlorophenyl)-7-chloro-pyrazolo[3,4][1,4]benzodiazepine
$^1$H nmr: (DMSO-d6,400 mHz) 12.09 (s, 1H, NH), 8.05 (s, 1H, NH), 7.68 (s, 1H), 7.56 (s, 1H), 7.52 (d, J=10 Hz, 1H), 7.48 (d, J=10 Hz, 1H), 7.19 (dd, J=2, 9 Hz, 1H), 6.78 (d, J=9 Hz, 1H), 6.27 (d, J=2 Hz, 1H).

1.9 Compound A9: $R^1=H$, $R^2=H$, $R^3=H$, $R^4=H$
5-phenyl-pyrazolo[3,4][1,4]benzodiazepine
$^1$H nmr: (DMSO-d6, 300 mHz) 12.04 (s, 1H), 7.77 (s, 1H), 7.58 (s, 1H), 7.32–7.47 (m, 5H), 7.22 (dt, J=2, 8 Hz,1 H), 6.92 (d, J=8 Hz,1 H), 6.76 (d, J=8 Hz, 1H), 6.67 (dd, J=1,8 Hz, 1H).

1.10 Compound A10: $R^1=H$, $R^2=F$, $R^3=H$, $R^4=H$
5-(2-fluorophenyl)-pyrazolo[3,4][1,4]benzodiazepine
$^1$H nmr: (DMSO-d6, 200 mHz) 12.00 (s, 1H, NH), 7.79 (s, 1H), 7.32–7.56 (m, 3H), 7.00–7.32 (m, 3H), 6.78 (d, J=6 Hz,1 H), 6.64 (t, J=6 Hz, 1 H), 6.48 (d, J=6 Hz, 1H).

1.11 Compound A11: $R^1=F$, $R^2=F$, $R^3=H$, $R^4=H$
5-(2-fluorophenyl)-7-fluoro-pyrazolo[3,4][1,4]benzodiazepine
$^1$H nmr: (DMSO-d6, 200 mHz) 12.10 (s, 1H, NH), 7.85 (s, 1H), 7.4–7.7 (m, 3H), 7.18–7.39 (m, 2H), 7.05 (m, 1H), 6.86 (m, 1H), 6.26 (br d, J=8 Hz, 1H).

1.12 Compound A12: $R^1=CH_3O$, $R^2=Cl$, $R^3=H$, $R^4=H$
5-(2-chlorophenyl)-7-methoxy-pyrazolo[3,4][1,4]benzodiazepine
$^1$H nmr: (DMSO-d6, 200 mHz) 12.00 (s, 1H, NH), 7.35–7.60 (m, 5H), 6.81 (d, J=8 Hz, 1H), 6.75 (d, J=8 Hz, 1H), 5.89 (s, 1H), 3.46 (s, 3H).

1.13 Compound A13: $R^1=NO_2$, $R^2=F$, $R^3=H$, $R^4=H$
5-(2-fluorophenyl)-7-nitro-pyrazolo[3,4][1,4]benzodiazepine
$^1$H nmr: (DMSO-d6, 300 mHz) 12.14 (s, 1H, NH), 9.06 (s, 1H, NH), 7.89 (dd, J=2, 9 Hz, 1H), 7.55 (s, 1H), 7.4–7.5 (m, 2H), 6.76 (d, J=9 Hz, IH).

1.14 Compound A14: $R^1=CH_3SO_2$, $R^2=H$, $R^3=H$, $R^4=H$
5-phenyl-7-methanesulfonyl-pyrazolo[3,4][1,4]benzodiazepine
$^1$H nmr: (DMSO-d6, 400 mHz) 12.18 (s, 1H, NH), 8.54 (s, 1H, NH), 7.72 (dd, J=2, 9 Hz, 1H), 7.64 (s, 1H), 7.43 (m, 5H), 7.14 (d, J=2, Hz, 1H), 7.06 (d, J=9 Hz, 1H), 3.01 (s, 3H).

1.15 Compound A15: $R^1=CN$, $R^2=F$, $R^3=H$, $R^4=H$
5-(2-fluorophenyl)-7-cyano-pyrazolo[3,4][1,4]benzodiazepine
$^1$H nmr: (DMSO-d6, 300 mHz) 12.16 (s, 1H, NH), 8.63 (s, 1H, NH), 7.59 (s, 1H), 7.4–7.58 (m, 3H), 7.2–7.37 (m, 2H), 6.82 (dd, J=2,8 Hz, 1H), 6.78 (s, 1H).

1.16 Compound A16: $R^1=NO_2$, $R^2=H$, $R^3=H$, $R^4=H$
5-phenyl-7-nitro-pyrazolo[3,4][1,4]benzodiazepine
$^1$H nmr: (DMSO-d6, 400 mHz) 12.19 (s, 1H, NH), 8.96 (s, 1H, NH), 8.03 (dd, J=2,9 Hz, 1H), 7.62 (s, 1H), 7.35–7.5 (m, 6H), 6.94 (d, J=9 Hz, 1H).

1.17 Compound A17: $R^1=NO_2$, $R^2=CF_3$, $R^3=H$, $R^4=H$
5-(2-trifluoromethylphenyl)-7-nitro-pyrazolo[3,4][1,4]benzodiazepine
$^1$H nmr: (DMSO-d6, 300 mHz) 12.12 (s, 1H, NH), 9.18 (s, 1H, NH), 7.45–7.9 (m, 6H), 7.00 (s, 1H), 6.71 (d, J=9 Hz, 1H).

1.18 Compound A18: $R^1=CO_2CH_3$, $R^2=H$, $R^3=H$, $R^4=H$
5-phenyl-7-carbomethoxy-pyrazolo[3,4][1,4]benzodiazepine
$^1$H nmr: (DMSO-d6, 300 mHz) 12.15 (s, 1H, NH), 8.42 (s, 1H, NH), 7.78 (dd, J=2,9 Hz, 1H), 7.62 (s, 1H), 7.35–7.45 (m, 5 H), 7.29 (d, J=2 Hz, 1H), 6.93 (d, J=9 Hz, 1H), 3.66 (s, 3H).

1.19 Compound A19: $R^1=I$, $R^2=F$, $R^3=H$, $R^4=H$
5-(2-fluorophenyl)-7-iodo-pyrazolo[3,4][1,4]benzodiazepine
$^1$H nmr: (DMSO-d6, 300 mHz) 12.09 (s, 1H, NH), 7.99 (s, 1H, NH), 7.58 (s, 1H), 7.4–7.55 (m, 3H), 7.19–7.35 (m, 2H), 6.76 (s, 1H), 6.62 (d, J=8 Hz, 1H).

1.20 Compound A20: $R^1=CO_2Et$, $R^2=F$, $R^3=H$, $R^4=H$
5-(2-fluorophenyl)-7-carboethoxy-pyrazolo[3,4][1,4]benzodiazepine
$^1$H nmr: (DMSO-d6, 300 mHz) 12.08 (s, 1H, NH), 8.50 (s, 1H, NH), 7.62 (d, J=8 Hz, 1H), 7.57 (s, 1H), 7.4–7.5 (m, 2H), 7.18–7.35 (m, 2H), 7.14 (s 1H), 6.80 (d, J=8 Hz, 1H), 4.15 (q, J=6 Hz, 2H), 1.17 (t, J=6 Hz, 3H).

1.21 Compound A21: $R^1=H$, $R^2=Cl$, $R^3=H$, $R^4=H$
5-(2-chlorophenyl)-pyrazolo[3,4][1,4]benzodiazepine
$^1$H nmr: (DMSO-d6, 300 mHz) 11.95 (s, 1H), 8.40 (s, 1H), 7.84 (s, 1H), 7.53 (s, 1H), 7.38–7.48 (m, 4H), 7.09 (t, J=8 Hz, 1H), 6.78 (d, J=8Hz, 1H), 6.61 (t, J=8 Hz, 1H), 6.34 (d, J=8 Hz, 1H).

Example 2

Conversion of Thiolactam 2 to Substituted Pyrazole 7 in Accordance with Schemes 2 and 3

2.1 Compound B1: $R^1=NO_2$, $R^2=Cl$, $R^3=$2-pyrrolyl, $R^4=H$; Scheme 2

3-(2-pyrrolyl)-5-(2-chlorophenyl)-7-nitro-pyrazolo[3,4][1,4]benzodiazepine

A mixture of 0.995 g (3 mmol) of thiolactam 2 ($R^1=NO_2$, $R^2=Cl$, $R^3=$2-pyrrolyl, $R^4=H$), 0.571 g (6 mmol) of pyrrole-2-carboxaldehyde, 0.383 g (4.5 mmol) (Aldrich) of piperidine and 10 mL of dimethoxyethane was stirred under argon for 2 hours. The mixture was taken up in ethyl acetate, and washed successively with 0.1 M sulfuric acid, water and then brine, dried over anhydrous sodium sulfate, filtered and concentrated under reduced pressure. The corresponding olefin 5 was isolated by silica gel chromatography (elution with hexane/ethyl acetate (1:1)) as a red solid (0.309 g) and used directly in the next step. Olefin 5 (0.309 g) was dissolved in 6 mL of dimethyl sulfoxide and reacted with 72.5 mg (2.2 mmol) of hydrazine under an argon atmosphere. After 20 min, the mixture was taken up in ethyl acetate and washed successively with water and brine, dried over anhydrous sodium sulfate, filtered and concentrated under reduced pressure to give a mixture of dihydropyrazoles 6 (0.296 g). The mixture of 6 was dissolved in dimethyl sulfoxide and heated in the presence of air at 130° C. for 2 hours, cooled, taken up in ethyl acetate, and washed successively with water and then brine. The extract was dried over anhydrous sodium sulfate, filtered and concentrated under reduced pressure. The product, Compound B1, 7 was purified by silica gel chromatography (elution with hexane-ethyl acetate 25/75).

$^1$H nmr: (DMSO-d6, 300 mHz) 12.12 (s, 1H, NH), 10.39 (s, 1H, NH), 9.07 (s, 1H, NH), 7.96 (dd, J=2, 8 Hz, 1 H), 7.4–7.65 (m, 4H), 7.15 (d, J=2 Hz, 1H), 6.90 (s, 1H), 6.79 (d, J=8 Hz, 1H), 6.48 (s, 1H), 6.12 (d, J=2Hz, 1H).

2.2 Compound B2: $R^1$=$NO_2$, $R^2$=Cl, $R^3$=$CO_2Et$, $R^4$=H; Scheme 3

3-carboethoxy-5-(2-chlorophenyl)-7-nitro-pyrazolo[3,4][1,4] benzodiazepine

A mixture of 5.0 g (15.1 mmol) of thiolactam 2 ($R^1$=$NO_2$, $R^2$=Cl), 6 mL of a 50% solution of ethyl glyoxylate in toluene, 4.5 mL (31 mmol) of diazabicycloundecane and 100 mL of dimethoxyethane was stirred under an argon atmosphere for 30 minutes at room temperature. The mixture was acidified with 0.005 M $H_2SO_4$, extracted with ethyl acetate. The combined extracts were dried over anhydrous sodium sulfate, filtered, and concentrated under reduced pressure. The aidol adduct 8 was obtained as a mixture of diastereomers (5.6 g) by silica gel chromatography (elution with hexane-ethyl acetate 60/40).

A mixture of 4.7 g (10.8 mmol) of aldol adduct 8 obtained above, 100 mL of pyridine and 6.9 mL (54.4 mmol) of chlorotrimethylsilane was stirred for 10 minutes at room temperature and then heated at 120° C. for 1.5 hours. The mixture was cooled, taken up in 1 L of ethyl acetate and washed successively with water and brine, and the ethyl acetate layer dried over anhydrous sodium sulfate. After filtration and evaporation of volatiles under reduced pressure, the crude residue was filtered through silica gel, eluting with hexane-ethyl acetate (1:1), to give 4.3 g of olefin 5.

A solution of 4.3 g of olefin 5, obtained above, in 210 mL of dichloromethane, was stirred with 0.68 mL (21.6 mmol) of anhydrous hydrazine for 30 min. The mixture was then partitioned between water, and the aqueous phase extracted with dichloromethane. The combined extracts were dried over anhydrous sodium sulfate, filtered and concentrated under reduced pressure. The residue, which contained a mixture of dihydropyrazoles 6, was dissolved in 50 mL of dimethylsulfoxide and heated at 130° C. in the presence of air for 3 hours. The reaction mixture was cooled, taken up in ethyl acetate and washed with water. The organic layer was dried over anhydrous sodium sulfate, filtered and concentrated under reduced pressure. The product was isolated by silica gel chromatography, eluting with hexane-ethyl acetate (40/60) to give 0.580 g of Compound B2 ($R^1$=$NO_2$, $R^2$=Cl, $R^3$=$CO_2Et$, $R^4$=H).

$^1$H nmr: (DMSO-d6, 400 mHz) 13.33 (s, 1H), 9.15 (s, 1H), 8.02 (dd, J=2, 9 Hz, 1H), 7.46–7.55 (m, 4H), 7.18 (d, J=2 Hz, 1H), 6.89 (d, J=9 Hz, 1H), 4.25 (q, J=7 Hz, 2H), 1,27 (t, J=7 Hz, 3H).

The following pyrazoles (compound 7) were prepared in accordance with scheme 2 or 3 as described above:

2.3 Compound B3: $R^1$=$NO_2$, $R^2$=Cl, $R^3$=$CH_3$, $R^4$=H (Scheme 2)

3-methyl-5-(2-chlorophenyl)-7-nitro-pyrazolo[3,4][1,4] benzodiazepine $^1$H nmr: (DMSO-d6, 300 mHz) 11.85 (s, 1H, NH), 9.04 (s, 1H, NH), 7.83 (dd, J=2, 9 Hz, 1 H), 7.39–7.52 (m, 4H), 7.05 (d, J=2 Hz, 1H), 6.69 (d, J=9 Hz,1H), 1.98 (s, 3H).

2.4 Compound B4: $R^1$=$NO_2$, $R^2$=Cl, $R^3$=$CH_2CH_3$, $R^4$=H (Scheme 2)

3-ethyl-5-(2-chlorophenyl)-7-nitro-pyrazolo[3,4][1,4] benzodiazepine $^1$H nmr: (DMSO-d6, 300 mHz) 11.91 (s, 1H, NH), 9.05 (s, 1H, NH), 7.85 (dd, J=2, 8 Hz,1H), 7.35–7.58 (m, 4H), 7.04 (d, J=2 Hz,1H), 6.71 (d, J=8 Hz, 1H), 2.41 (q, J=7 Hz, 2H), 1.06 (t, J=7 Hz, 3H).

2.5 Compound B5: $R^1$=$NO_2$, $R^2$=Cl, $R^3$=$CH_2CH_2Ph$, $R^4$=H (Scheme 2)

3-(2-phenylethyl)-5-(2-chlorophenyl)-7-nitro-pyrazolo[3,4][1,4] benzodiazepine $^1$H nmr: (DMSO-d6, 200 mHz) 11.95 (s, 1H, NH), 9.05 (s, 1H, NH), 7.82 (dd, J=2, 8 Hz, 1H), 7.05–7.60 (m, 10H), 6.70 (d, J=8 Hz, 1H), 2.82 (m, 2H), 2.64 (m, 2H).

2.6 Compound B6: $R^1$=$NO_2$, $R^2$=Cl, $R^3$=i-Pr, $R^4$=H (Scheme 2)

3-(1-methylethyl)-5-(2-chlorophenyl)-7-nitro-pyrazolo[3,4][1,4]benzodiazepine $^1$H nmr: (DMSO-d6, 300 mHz) 11.90 (s, 1H, NH), 9.02 (s, 1H, NH), 7.84 (dd, J=2, 9 Hz, 1H), 7.35–7.55 (m, 4H), 7.04 (d, J=2 Hz, 1H), 6.74 (d, J=9 Hz, 1H), 2.86 (sept, J=9 Hz, 1H), 1.14 (d, J=9 Hz, 6H).

2.7 Compound B7: $R^1$=CN, $R^2$=F, $R^3$=$CH_3$, $R^4$=H (Scheme 2)

3-methyl-5-(2-fluorophenyl)-pyrazolo[3,4][1,4]benzodiazepine-7-carbonitrile $^1$H nmr: (DMSO-d6, 300 mHz) 12.05 (s, 1H, NH), 8.55 (s, 1H, NH), 7.45 (m, 3H), 7.25 (m, 2H), 6.78 (d, J=8 Hz, 1H), 6.71 (s, 1H), 2.03 (s, 3H).

2.8 Compound B8: $R^1$=$NO_2$, $R^2$=Cl, $R^3$=$CH_2Ph$, $R^4$=H (Scheme 2)

3-(phenylmethyl)-5-(2-chlorophenyl)-7-nitro-pyrazolo[3,4][1,4]benzodiazepine $^1$H nmr: (DMSO-d6, 300 mHz) 12.08 (s, 1H, NH), 9.08 (s, 1H), 7.85 (d, J=9 Hz, 1H), 7.40–7.56 (m, 4H), 7.16–7.34 (m, 5H), 7.06 (brs, 1H), 6.71 (d, J=9 Hz, 1H), 3.71 (s, 2H).

2.9 Compound B9: $R^1$=$CO_2Et$, $R^2$=F, $R^3$=$CH_3$, $R^4$=H (Scheme 2)

3-methyl-5-(2-fluorophenyl)-7-carboethoxy-pyrazolo[3,4][1,4]benzodiazepine $^1$H nmr: (DMSO-d6, 300 mHz) 11.81 (s, 1H), 8.37 (s, 1H), 7.59 (dd, J=2, 9 Hz, 1H), 7.39–7.51 (m, 2H), 7.16–7.31 (m, 2H), 7.09 (s, 1H), 6.74 (d, J=9 HZ, 1H), 4.08 (q, J=7 Hz, 2H), 2.04 (s, 3H), 1.12 (t, J=7 Hz, 3H).

2.10 Compound B10: $R^1$=$NO_2$, $R^2$=Cl, $R^3$=5-(4-Me)-pyrazolyl, $R^4$=H (Scheme 2)

3-(4-methylpyrazol-5-yl)-5-(2-chlorophenyl)-7-nitro-pyrazolo[3,4][1,4]benzodiazepine $^1$H nmr: (DMSO-d6, 400 mHz) 12.58 (s, 1H), 9.26 (s, 1H), 8.75 (brs, 1H), 7.95 (d, J=8 Hz, 1H), 7.42–7.6 (m, 5H), 7.12 (s, 1H), 6.81 (d, J=8 Hz, 1H) 2.32 (s, 3H).

2.11 Compound B11: $R^1$=$NO_2$, $R^2$=Cl, $R^3$=$CH_2$-iPr, $R^4$=H (Scheme 2)

3-(2-methylpropyl)-5-(2-chlorophenyl)-7-nitro-pyrazolo[3,4][1,4]benzodiazepine $^1$H nmr: (DMSO-d6, 400 mHz) 11.91 (s,1 H), 9.06 (s, 1H), 7.87 (dd, J=2, 9 Hz, 1H), 7.4–7.56 (m, 4H), 7.08 (d, J=2 Hz, 1H), 6.74 (d, J=9 Hz, 1H),
2.28 (d, J=7 Hz, 2H), 1.89 (n, J=7 Hz, 1H), 0.88 (d, J=7 Hz, 6H).

2.12 Compound B12: $R^1$=$NO_2$, $R^2$=Cl, $R^3$=$CF_3$, $R^4$=H (Scheme 3)

3-trifluoromethyl-5-(2-chlorophenyl)-7-nitro-pyrazolo[3,4][1,4]benzodiazepine $^1$H nmr: ($CDCl_3$+DMSO-d6, 300 mHz) 7.98 (dd, J=2, 9 Hz, 1H), 7.2–7.6 (m, 6H), 7.02 (br s, 1H), 6.62 (d, J=9 Hz, 1H).

2.13 Compound B13: $R^1$=$NO_2$, $R^2$=Cl, $R^3$=1-thiazolyl, $R^4$=H (Scheme 3)
3-(1-thiazolyl)-5-(2-chlorophenyl)-7-nitro-pyrazolo[3,4][1,4]benzodiazepine
$^1$H nmr: (DMSO-d6, 300 mHz) 13.08 (s, 1H), 9.21 (s, 1H), 7.88–7.92 (m, 2H), 7.84 (d, J=3 Hz, 1H), 7.42–7.62 (m, 4H), 7.12 (d, J=2 Hz, 1H), 6.79 (d, J=8 Hz, 1H).

2.14 Compound B14: $R^1$=$NO_2$, $R^2$=Cl, $R^3$=4-imidazolyl, $R^4$=H (Scheme 2)
3-(4-imidazolyl)-5-(2-chlorophenyl)-7-nitro-pyrazolo[3,4][1,4]benzodiazepine
$^1$H nmr: (DMSO-d6, 400 mHz) 12.33 (s, 1H), 12.29 (s, 1H), 9.07 (s, 1H), 7.90 (dd, J=2, 9 Hz,1H), 7.76 (s, 1H), 7.44–7.63 (m, 4H), 7.35 (s, 1H), 7.11 (d, J=2 Hz, 1H), 6.78 (d, J=9 Hz, 1H).

2.15 Compound B15: $R^1$=$NO_2$, $R^2$=Cl, $R^3$=2-pyrazolyl, $R^4$=H (Scheme 2)
3-(2-pyrazolyl)-5-(2-chlorophenyl)-7-nitro-pyrazolo[3,4][1,4]benzodiazepine
$^1$H nmr: (DMSO-d6, 300 mHz) 13.11 (s, 1H), 12.48 (s, 1H), 9.12 (s, 1H), 7.93 (d, J=9 Hz, 1H), 7.76 (s, 1H), 7.39–7.60 (m, 4H), 7.11 (s, 1H), 6.78 (=9 Hz, 1H), 6.59 (s, 1H).

2.16 Compound B16: $R^1$=$NO_2$, $R^2$=Cl, $R^3$=3-pyrazolyl, $R^4$=H (Scheme 2)
3-(3-pyrazolyl)-5-(2-chlorophenyl)-7-nitro-pyrazolo[3,4][1,4]benzodiazepine
$^1$H nmr: (DMSO-d6, 300 mHz) 13.09 (s, 1H), 12.31 (s, 1H), 9.13 (s, 1H), 7.80–8.05 (m, 4H), 7.40–7.62 (m, 3H), 7.13 (s, 1H), 6.78 (d, J=9 Hz, 1H).

2.17 Compound B17: $R^1$=$NO_2$, $R^2$=Cl, $R^3$=CH(Me)$CH_2$Me, $R^4$=H (Scheme 2)
3-(1-methylpropyl)-5-(2-chlorophenyl)-7-nitro-pyrazolo[3,4][1,4]benzodiazepine
$^1$H nmr: (DMSO-d6, 300 mHz) 11.90 (s, 1H), 9.04 (s, 1H), 7.85 (dd, J=2, 9 Hz, 1H), 7.38–7.55 (m, 4H), 7.05 (d, J=2 Hz, 1 H), 6.72 (d, J=9 Hz, 1H), 2.65 (m, 1H), 1.52 (m, 2H), 1.13 (d, J=7 Hz, 3H), 0.79 (t, J=8 Hz, 3H).

2.18 Compound B18: $R^1$=MeO, $R^2$=Cl, $R^3$=$CH_3$, $R^4$=H (Scheme 2)
3-methyl-5-(2-chlorophenyl)-7-methoxy-pyrazolo[3,4][1,4]benzodiazepine
$^1$H nmr: (DMSO-d6, 300 mHz) 11.69 (s, 1H), 7.34–7.50 (m, 5H), 6.77 (dd, J=2, 9 Hz, 1H), 6.72 (d, J=9 Hz, 1H), 5.86 (d, J=9 Hz, 1H), 5.86 (d, J=2 Hz, 1H), 3.44 (s, 3H), 2.05 (s, 3H).

2.19 Compound B19: $R^1$=Cl, $R^2$=H, $R^3$=$CH_3$, $R^4$=H (Scheme 2)
3-methyl-5-phenyl-7-chloro-pyrazolo[3,4][1,4]benzodiazepine
$^1$H nmr: (DMSO-d6, 400 mHz) 11.85 (s, 1H), 7.90 (s, 1H), 7.46–7.52 (m, 2H), 7.39–7.44 (m, 3H), 7.29 (dd, J=2, 9 Hz, 1H), 6.92 (d, J=9 Hz, 1H), 6.62 (d, J=2 Hz, 1H), 2.16 (s, 3H).

2.20 Compound B20: $R^1$=Cl, $R^2$=Cl, $R^3$=$CH_3$, $R^4$=H (Scheme 2)
3-methyl-5-(2-chlorophenyl)-7-chloro-pyrazolo[3,4][1,4]benzodiazepine
$^1$nmr: (DMSO-d6, 300 mHz) 11.78 (s, 1H), 7.95 (s, 1H), 7.38–7.55 (m, 4H), 7.17 (dd, J=2, 9 Hz,1H), 6.75 (d, J=9 Hz, 1H), 6.22 (d, J=2 Hz, 1H), 2.03 (s, 3H).

2.21 Compound B21: $R^1$=H, $R^2$=F, $R^3$=$CH_3$, $R^4$=H (Scheme 2)
3-methyl-5-(2-fluorophenyl)-pyrazolo[3,4][1,4]benzodiazepine
$^1$H nmr: (DMSO-d6, 300 mHz) 11.75 (s, 1H), 7.69 (s, 1H), 7.36–7.52 (m, 2H), 7.04–7.30 (m, 3H), 6.77 (d, J=8 Hz, 1H), 6.63 (t, J=8 Hz, 1H), 6.50 (d, J=8 Hz, 1H), 2.07 (s, 3H).

2.22 Compound B22: $R^1$=F, $R^2$=H, $R^3$=$CH_3$, $R^4$=H (Scheme 2)
3-methyl-5-phenyl-7-fluoro-pyrazolo[3,4][1,4]benzodiazepine
$^1$H nmr: (DMSO-d6, 300 mHz) 11.85 (s, 1H), 7.70 (s, 1H), 7.46–7.55 (m, 2H), 7.35–7.43 (m, 2H), 7.11 (dt, J=3, 9 Hz, 1H), 6.92 (dd, J=5, 9 Hz, 1H), 6.41 (dd, J=3, 10 Hz, 1H), 2.14 (s, 3H).

2.23 Compound B23: $R^1$=$NO_2$, $R^2$=Cl, $R^3$=phenyl, $R^4$=H (Scheme 2)
3-phenyl-5-(2-chlorophenyl)-7-nitro-pyrazolo[3,4][1,4]benzodiazepine
$^1$H nmr: (DMSO-d6, 400 mHz) 12.65 (s, 1H), 9.18 (s, 1H), 7.95 (dd, J=2, 9 Hz, 1H), 7.78 (d, J=8 Hz, 2H), 7.32–7.63 (m, 7H), 7.14 (d, J=2 Hz, 1H), 6.85 (d, J=9 Hz, 1H).

2.24 Compound B24: $R^1$=$NO_2$, $R^2$=Cl, $R^3$=n-propyl, $R^4$=H (Scheme 2)
3-propyl-5-(2-chlorophenyl)-7-nitro-pyrazolo[3,4][1,4]benzodiazepine
$^1$H nmr: (DMSO-d6, 400 mHz) 11.91 (s, 1H), 9.06 (s, 1H), 7.86 (d, J=8 Hz, 1H), 7.41–7.53 (m, 4H), 7.08 (s, 1H), 6.72 (d, J=8 Hz, 1H), 2.38 (t, J=8 Hz, 2H), 1.54 (tq, J=8, 7 Hz, 2H), 0.88 (t, J=7 Hz, 3H).

Compound B25: $R^1$=$NO_2$, $R^2$=Cl, $R^3$=cyclopropyl, $R^4$=H (Scheme 2)
3-cyclopropyl-5-(2-chlorophenyl)-7-nitro-pyrazolo[3,4][1,4]benzodiazepine
$^1$H nmr: (DMSO-d6, 400 mHz) 11.72 (s, 1H), 9.05 (s, 1H), 7.87 (dd, J=2, 9 Hz, 1H), 7.41–7.55 (m, 4H), 7.08 (d, J=2Hz, 1H), 6.72 (d, J=9 Hz, 1H), 1.79 (p, J=7 Hz, 1H), 0.88 (d, J=7 Hz, 4H).

2.26 Compound B26: $R^1$=F, $R^2$=F, $R^3$=$CH_3$, $R^4$=H (Scheme 2)
3-methyl-5-(2-fluorophenyl)-7-fluoro-pyrazolo[3,4][1,4]benzodiazepine
$^1$H nmr: (DMSO-d6, 300 mHz) 11.82 (s, 1H), 7.76 (s, 1H), 7.41–7.58 (m, 2H), 7.18–7.35 (m, 2H), 7.05 (dt, J=3, 9 Hz, 1H), 6.84 (dd, J=6, 9 Hz, 1H), 6.25 (dd, J=3, 9 Hz, 1H), 2.08 (s, 3H).

2.27 Compound B27: $R^1$=$NO_2$, $R^2$=H, $R^3$=$CH_3$, $R^4$=H (Scheme 2)
3-methyl-5-phenyl-7-nitro-pyrazolo[3,4][1,4]benzodiazepine 2.28 Compound B28: $R^1$=H, $R^2$=H, $R^3$=$CH_3$, $R^4$=H (Scheme 2)
3-methyl-5-phenyl-pyrazolo[3,4][1,4]benzodiazepine
$^1$H nmr: (DMSO-d6, 300 mHz) 11.78 (s, 1H), 7.66 (s, 1H), 7.47 (m, 2H), 7.39 (m, 3H), 7.20 (dt, J=1, 8 Hz, 1H), 6.88 (d, J=8 Hz, 1H), 6.75 (t, J=8 Hz, 1H), 6.68 (dt, J=1, 8 Hz, 1H), 2.14 (s, 3H).

2.29 Compound B29: $R^1$=I, $R^2$=F, $R^3$=$CH_3$, $R^4$=H (Scheme 2)
3-methyl-5-(2-fluorophenyl)-7-iodo-pyrazolo[3,4][1,4]benzodiazepine
$^1$H nmr: (DMSO-d6, 300 mHz) 11.81 (s, 1H), 7.90 (s, 1H), 7.39–7.57 (m, 3H), 7.18–7.36 (m, 2H), 6.75 (s, 1H), 6.59 (d, J=9 Hz, 1H), 2.07 (s, 3H)

2.30 Compound B30: $R^1$=H, $R^2$=Cl, $R^3$=$CH_3$, $R^4$=H (Scheme 2)
3-methyl-5-(2-chlorophenyl)-pyrazolo[3,4][1,4]benzodiazepine 2.31 Compound B31: $R^1$=$NO_2$, $R^2$=F, $R^3$=$CH_3$, $R^4$=H (Scheme 2)
3-methyl-5-(2-fluorophenyl)-7-nitro-pyrazolo[3,4][1,4]benzodiazepine
$^1$H nmr: (DMSO-d6, 300 mHz) 11.90 (s, lH), 9.00 (s, lH), 7.87 (dd, J=3, 9 Hz, 1H), 7.47 (m, 3H), 7.18–7.32 (m, 3H), 6.73 (d, J=9 Hz, 1H), 2.02 (s, 3H).

2.32 Compound B32: $R^1$=Cl, $R^2$=F, $R^3$=CH$_3$, $R^4$=H (Scheme 2)

3-methyl-5-(2-fluorophenyl)-7-chloro-pyrazolo[3,4][1,4]benzodiazepine $^1$H nmr: (DMSO-d6, 300 mHz) 11.81 (s, 1H), 7.96 (s, 1H), 7.40–7.55 (m, 2H), 7.17–7.32 (m, 3H), 6.79 (d, J=9 Hz, 1H), 6.42 (s, 1H), 2.08 (s, 3H).

2.33 Compound B33: $R^1$=I, $R^2$=H, $R^3$=CH$_3$, $R^4$=H (Scheme 2)

3-methyl-5-phenyl-7-iodo-pyrazolo[3,4][1,4]benzodiazepine $^1$H nmr: (DMSO-d6, 300 mHz) 11.82 (s, 1H), 7.85 (s, 1H), 7.36–7.55 (m, 6H), 6.91 (d, J=2 Hz, 1H), 6.70 (d, J=9 Hz, 1H), 2.15 (s, 3H).

2.34 Compound B34: $R^1$=Br, $R^2$=H, $R^3$=CH$_3$, $R^4$=H (Scheme 2)

3-methyl-5-phenyl-7-bromo-pyrazolo[3,4][1,4]benzodiazepine $^1$H nmr: (DMSO-d6, 300 mHz) 7.89 (s, 1H), 7.49 (m, 2H), 7.38 (m, 4H), 6.85 (d, J=9 Hz, 1H), 6.74 (d, J=2 Hz, 1H), 2.15 (s, 3H).

2.35 Compound B35: $R^1$=CN, $R^2$=F, $R^3$=—CH$_2$OH, $R^4$=H (Shceme 3)

3-hydroxymethyl-5-(2-fluorophenyl)-pyrazolo[3,4][1,4]-benzodiazepine-7-carbonitrile.

Example 3

Functional Group Modification in Accordance with Scheme 4

As mentioned above with reference to Scheme 4, certain compounds may be easily obtained by transformation of existing functional groups. Several of these transformations are further exemplified below.

A. Substitution of Iodo by Carbonyl: $R^1$=I to $R^1$=CONRR'

3.1 Compound C1: $R^1$=CON(—CH$_2$CH$_2$—O—CH$_2$CH$_2$—), $R^2$=F, $R^3$=H, R 5-(2-fluorophenyl)-7-morpholinylcarbonyl-pyrazolo[3,4][1,4]benzodiazepine A mixture of 0.0712 g (0.17 mmol) of pyrazole 4 ($R^1$=I, $R^2$=F, $R^3$=H, $R^4$=H), 0.0082 g (0.0012 mmol) of bis triphenylphosphine palladium dichloride catalyst, 1 mL of morpholine was stirred and heated (75° C.) under an atmosphere of carbon monoxide for 90 minutes. The mixture was cooled, and then purified by chromatography on reverse phase silica gel (gradient elution with water-acetonitrile) to give 0.06 g of Compound C1 (pyrazole 4 wherein $R^1$=CON(—CH$_2$CH$_2$—O—CH$_2$CH$_2$—), $R^2$=F, $R^3$=H, $R^4$=H).

$^1$H nmr: (DMSO-d6, 300 mHz) 12.05 (s, 1H, NH), 8.18 (s, 1H, NH), 7.59 (s, 1H), 7.4–7.5 (m, 2H), 7.18–7.35 (m, 3H), 6.84 (d, J=9 Hz, 1H), 3.25 (m, 8H).

The following compounds were prepared using method A above:

3.2 Compound C2: $R^1$=CONHCH$_2$CH$_2$OH, $R^2$=F, $R^3$=H, $R^4$=H

N-(2-hydroxyethyl)-5-(2-fluorophenyl)-pyrazolo[3,4][1,4]benzodiazepine-7-carboxamide $^1$H nmr: (DMSO-d6, 300 mHz) 12.08 (s, 1H, NH), 8.20 (s, 1H, NH), 8.16 (m, 1H, NH), 7.61 (d, J=9 Hz, 1H), 7.57 (s, 1H), 7.4–7.5 (m, 2H), 7.14–7.3 (m, 2H), 7.11 (s, 1H), 6.89 (d, J=9 Hz, 1H), 4.63 (m, 1H, OH), 3.40 (m, 2H), 3.18 (m, 2H).

3.3 Compound C3: $R^1$=CON(CH$_2$CH$_2$OH)$_2$, $R^2$=F, $R^3$=H, $R^4$=H

N,N-bis-(2-hydroxyethyl)-5-(2-fluorophenyl)-pyrazolo[3,4][1,4]benzodiazepine-7-carboxamide $^1$H nmr: (DMSO-d6, 300 mHz) 12.10 (s, 1H, NH), 8.11 (s, 1H, NH), 7.59 (s, 1H), 7.4–7.52 (m, 2H), 7.15–7.3 (m, 3H), 6.80 (d, J=9 Hz, 1H), 6.58 (s, 1H), 4.65 (m, 2H, OH), 3.30 (m, 8H).

B. Reduction of the Nitro to Amino: $R^1$=NO$_2$ to $R^1$=NH$_2$ 3.4 Compound C4: $R^1$=NH$_2$, $R^2$=Cl, $R^3$=CH$_3$, $R^4$=H 3-methyl-5-(2-chlorophenyl)-7-amino-pyrazolo[3,4][1,4]benzodiazepine A solution of 0.20 g (0.57 mmol) of pyrazole 7 ($R^1$=NO$_2$, $R^2$=Cl, $R^3$=CH$_3$, $R^4$=H) in 8 mL of ethanol was stirred at room temperature under a hydrogen atmosphere with Raney nickel (0.5 mL of a 50% slurry in water, washed with ethanol just prior to use). After 4 hours, the mixture was filtered, and concentrated under reduced pressure to give 0.177 g of Compound C4 (amino derivative 7 wherein $R^1$=NO$_2$, $R^2$=Cl, $R^3$=CH$_3$, $R^4$=H). mp. 260–263° C.

$^1$H nmr: (DMSO-d6, 300 mHz) 11.62 (s, 1H), 7.38–7.47 (m, 4H), 7.07 (s, s, 1H), 6.53 (d, J=8 Hz, 1H), 6.38 (dd, J=2, 9 Hz,1H), 5.74 (d, J=2 Hz, 1H), 4.52 (s, 2H), 2.06 (s, 3H).

The following compounds were prepared using method B above:

3.5 Compound C5: $R^1$=NH$_2$, $R^2$=Cl, $R^3$=H, $R^4$=H 5-(2-chlorophenyl)-7-amino-pyrazolo[3,4][1,4]benzodiazepine $^1$H nmr: (CD$_3$OD, 300 mHz) 7.35–7.55 (m, 5 H), 6.72 (dd, J=3, 7 Hz, 1H), 6.62 (d, J=7 Hz, 1H), 6.13 (d, J=3 Hz, 1H).

3.6 Compound C6: $R^1$=NH$_2$, $R^2$=Cl, $R^3$=I-Pr, $R^4$=H 3-(1-methylethyl)-5-(2-chlorophenyl)-7-amino-pyrazolo[3,4][1,4]benzodiazepine $^1$H nmr: (DMSO-d6, 300 mHz) 11.65 (2, 1 H), 7.38–7.4 (m, 4H), 7.08 (s, 1H), 6.75 (d, J=8 Hz, 1H), 6.39 (dd, J=2, 8 Hz, 1H), 5.74 (d, J=2 Hz, 1H), 2.98 (sept, J=7 Hz, 1H), 1.18 (d, J=7 Hz, 6H).

C. Derivitization of Amino Compounds: $R^1$=NH$_2$ to $R^1$=NHR' (as Defined in Scheme 4 supra)

3.7 Compound C7: $R^1$=NHAc, $R^2$=Cl, $R^3$=CH$_3$, $R^4$=H

N-(3-methyl-5-(2-chlorophenyl)-pyrazolo[3,4][1,4]benzodiazepin-7-yl)-acetamide

A suspension of 0.323 g (1 mmol) of pyrazole 7 ($R^1$=NH$_2$, $R^2$=Cl, $R^3$=CH$_3$, $R^4$=H) in 20 mL of dichloromethane was reacted with 0.112 g (1.1 mmol) of acetic anhydride under an inert atmosphere at room temperature for 2 hours. The mixture was then diluted with ethyl acetate and washed successively with water and brine. The aqueous layers were extracted with ethyl acetate, and the combined extracts dried over anhydrous sodium sulfate, filtered and concentrated under reduced pressure. The product was isolated by silica gel chromatography eluting with hexane-ethyl acetate (30/70) to give 0.175 g of Compound C7.

$^1$H nmr: (DMSO-d6, 300 mHz) 11.71 (s, 1H), 9.56 (s, 1H), 7.56 (s, 1H), 7.38–7.57 (m, 5H), 6.67 (d, J=8 Hz, 1H), 6.57 (d, J=2 Hz, 1H), 2.05 (s, 3H), 1.83 (s, 3H).

The following compounds were prepared analogously to Compound C7 in accordance with Method C above:

3.8 Compound C8: $R^1$=AcryloylNH, $R^2$=Cl, $R^3$=CH$_3$, $R^4$=H
N-(3-methyl-5-(2-chlorophenyl)-pyrazolo[3,4][1,4]benzodiazepin-7-yl)-2-propenamide $^1$H nmr: (DMSO-d6, 300 mHz) 11.71 (s, 1H), 9.78 (s, 1H), 7.63 (s, 1H), 7.52 (dd, J=2, 9 Hz, 1H), 7.35–7.50 (m, 4H), 6.71 (d, J=9 Hz, 1H), 6.69 (d, J=2 Hz, 1H), 6.23 (dd, J=10, 18 Hz, 1H), 6.08 (dd, J=2, 18 Hz,1H), 5.60 (dd, J=2, 10 Hz, 1H), 2.05 (s, 3H).

3.9 Compound C9: $R^1$=CH$_3$SO$_2$NH, $R^2$=Cl, $R^3$=CH$_3$, $R^4$=H
N-(3-methyl-5-(2-chlorophenyl)-pyrazolo[3,4][1,4]benzodiazepin-7-yl)-methanesulfonamide A mixture of 0.323 g (1 mmol) of pyrazole 7 ($R^1$=NH$_2$, $R^2$=Cl, $R^3$=CH$_3$, $R^4$=H), 0.122 g (1 mmol) of 4-dimethylaminopyridine and 5 mL of tetrahydrofuran was stirred under an inert atmosphere at room temperature for 2 hours. The mixture was diluted with ethyl acetate and washed successively with water and brine, with reextraction of the aqueous phases with ethyl acetate. The combined ethyl acetate extracts were dried over anhydrous sodium sulfate, filtered and concentrated under reduced pressure. The product was isolated by silica gel chromatography eluting with hexane-ethyl acetate (10/90) to give 0.244 g of Compound C9 (pyrazole 7 where $R^1$=CH$_3$SO$_2$NH, $R^2$=Cl, $R^3$=CH$_3$, $R^4$=H) (recrystallization from ethyl acetate) mp 196–198° C.

$^1$H nmr: (DMSO-d6, 300 mHz) 11.74 (s, 1H), 9.12 (s, 1H), 7.71 (s, 1H), 7.36–7.46 (m, 4H), 6.94 (dd, J=2, 8 Hz, 1H), 6.72 (d, J=8 Hz, 1H), 6.31 (d, J=2 Hz, 1H), 2.70 (s, 3H), 2.05 (s, 3H).

D. Aminolysis of $R^3$=CO$_2$Et to $R^3$=CONRR'

3.10 Compound C10: $R^1$=NO$_2$, $R^2$=Cl, $R^3$=CONH$_2$, $R^4$=H
5-(2-chlorophenyl)-7-nitro-pyrazolo[3,4][1,4]benzodiazepine-3-carboxamide 0.15 g (0.36 mmol) of pyrazole 7 ($R^1$=NO$_2$, $R^2$=Cl, $R^3$=CO$_2$Et, $R^4$=H) was stirred with a solution of ammonia (15 mL) in ethanol (50 mL) at room temperature for 48 hours. Volatiles were removed under reduced pressure and the product purified by silica gel chromatography. Elution with ethyl acetate-isopropanol (95/5) gave 0.074 g of Compound C10 (pyrazole 7' wherein $R^1$=NO$_2$, $R^2$=Cl, $R^3$=CONH$_2$, $R^4$=H), as a solid. mp>340° C. (recrystallization from ethyl acetate).

$^1$H nmr: (DMSO-d6, 400 mHz) 12.95 (br s, 1H), 9.23 (br s, 1H), 7.92 (d, J=8 Hz, 1H), 7.81 (s, 1H), 7.45–7.61 (m, 4H), 7.21 (s, 1H), 7.08 (s,1H), 6.75 (d, J=8 Hz, 1H).

The following compounds were prepared analogously to Compound C10 using Method D above:

3.11 Compound C11: $R^1$=NO$_2$, $R^2$=Cl, $R^3$=CONMe$_2$, $R^4$=H
N,N-dimethyl-5-(2-chlorophenyl)-7-nitro-pyrazolo[3,4][1,4]benzodiazepine-3-carboxamide $^1$H nmr: (DMSO-d6, 300 mHz) 12.65 (s, 1H), 9.18 (s, 1H), 7.91 (d, J=9 Hz, 1H), 7.41–7.55 (m, 4H), 7.08 (s, 1H), 6.75 (d, J=9 Hz, 1H), 3.01 (s, 3H), 2.88 (s, 3H).

3.12 Compound C12: $R^1$=NO$_2$, $R^2$=Cl, $R^3$=CONHNH$_2$, $R^4$=H
N-amino-5-(2-chlorophenyl)-7-nitro-pyrazolo[3,4][1,4]benzodiazepine-3-carboxamide $^1$H nmr: (DMSO-d6, 300 mHz) 13.02 (s, 1H), 9.19 (s, 1H), 8.58 (t, J=5 Hz, 1H), 7.91 (dd, J=2, 9 Hz, 1H), 7.41–7.62 (m, 4H), 7.09 (d, J=2 Hz, 1H), 6.75 (d, J=9 Hz, 1H), 4.54 (d, J=5 Hz, 2H).

E. Reduction of $R^3$=CO$_2$Et to $R^3$=CHO and $R^3$=CH$_2$OH 3.13 Compound C13: $R^1$=NO$_2$, $R^2$=Cl, $R^3$=CHO, $R^4$=H; and Compound C14 $R^1$=NO$_2$, $R^2$=Cl, $R^3$=CH$_2$OH, $R^4$=H A mixture of 0.48 g (1.17 mmol) of pyrazole 7 ($R^1$=NO$_2$, $R^2$=Cl, $R^3$=CO$_2$Et, $R^4$=H) and 30 mL of tetrahydrofuran at −15° C. under an inert atmosphere was treated with 1.52 mL of a 1 M solution of lithium aluminum hydride in tetrahydrofuran for 30 minutes. The mixture was then diluted with ethyl acetate and washed successively with aqueous sodium potassium sulfate and brine, reextracting the organic washes with ethyl acetate. The combined ethyl acetate extracts were dried over anhydrous sodium sulfate, filtered and concentrated under reduced pressure. Purification by silica gel chromatography, eluting with hexane-ethyl acetate gave 0.21 g of Compound C13 (pyrazole 7' wherein $R^1$=NO$_2$, $R^2$=Cl, $R^3$=CHO, $R^4$=H) as a red solid, and 0.11 g of Compound C14 (pyrazole 7' wherein $R^1$=NO$_2$, $R^2$=Cl, $R^3$=CH$_2$OH, $R^4$=H), also as a red solid.

Compound C13:
5-(2-chlorophenyl)-7-nitro-pyrazolo[3,4][1,4]benzodiazepine-3-carboxaldehyde $^1$H nmr: (DMSO-d6, 300 mHz) 13.29 (s, 1H), 9.66 (s, 1H), 9.27 (s, 1H), 7.96 (dd, J=2, 9 Hz, 1H), 7.45–7.59 (m, 4H), 7.13 (d, J=2 Hz, 1H), 6.79 (d, J=9 Hz, 1H).

Compound C14:
3-hydroxymethyl-5-(2-chlorophenyl)-7-nitro-pyrazolo[3,4][1,4]benzodiazepine $^1$H nmr: (DMSO-d6, 300 mHz) 12.11 (s, 1H), 9.08 (s, 1H), 7.85 (dd, J=2, 9 Hz, 1H), 7.42–7.50 (m, 4H), 7.06 (d, J=2 Hz, 1H), 6.71 (d, J=9 Hz, 1H), 5.23 (t, J=5 Hz, 1H), 4.27 (d, J=5 Hz, 2H).

F. Reductive Amination of an Aldehyde: $R^3$=CHO to $R^3$=CH$_2$NR$^2$ 3.14 Compound C15: $R^1$=NO$_2$, $R^2$=Cl, $R^3$=CH$_2$NMe$_2$, $R^4$=H
-(N, N-dimethylaminomethyl)-5-(2-chlorophenyl)-7-nitro-pyrazolo[3,4][1,4]benzodiazepine A suspension of 0.142 g (0.39 mmol) of pyrazole 7 ($R^1$=NO$_2$, $R^2$=Cl, $R^3$=CHO, $R^4$=H), 0.0631 g (0.78 mmol) of dimethylamine hydrochloride, 0.11 mL (0.78 mmol) of triethylamine, 0.165 g (1 mmol) of sodium triacetoxyborohydride, 0.2 of 4A molecular sieves and 20 mL of dichloromethane was stirred under an inert atmosphere for 3 hours. The mixture was filtered, diluted with ethyl acetate and washed successively with water and brine, reextracting the aqueous phases with ethyl acetate. The combined ethyl acetate extracts were dried over anhydrous sodium sulfate, filtered and concentrated under reduced pressure. Purification by reverse phase silica gel chromatography (gradient elution with water-acetonitrile-trifluoroacetic acid) gave 0.147 g of Compound C15 (pyrazole 7' wherein $R^1$'NO$_2$, $R^2$=Cl, $R^3$=CH$_2$NMe$_2$, $R^4$=H) as the trifluoroacetate salt.

$^1$H nmr: (DMSO-d6, 300 mHz) 12.54 (s, 1H), 9.92 (s, 1H), 9.25 (s, 1H), 7.91 (dd, J=2, 8 Hz, 1H), 7.45–7.55 (m, 4H), 7.10 (d, J=2 Hz, 1H), 6.76 (d, J=8 Hz, 1H), 4.08 (s, 2H), 2.75 (s, 6H).

G. Alkylation of Alcohols: $R^3$=CH$_2$OH to $R^3$=CH$_2$OCH$_3$ 3.15 Compound C16: $R^1$=NO$_2$, $R^2$=Cl, $R^3$=CH$_2$OCH$_3$, $R^4$=H
3-methoxymethyl-5-(2-chlorophenyl)-7-nitro-pyrazolo[3,4][1,4]benzodiazepine A mixture of 0.075 g (0.2 mmol) of pyrazole 7 ($R^1$=NO$_2$, $R^2$=Cl, $R^3$=CH$_2$OH, $R^4$=H), 0.2 g of silica gel and 20 mL of tetrahydrofuran was stirred with a solution of diazomethane in ether (50 mL, ca. 9.2 mmol). After 2 hours the mixture was filtered, concentrated under reduced pressure. The product was purified by chromatography on silica gel, eluting with hexane-ethyl acetate, to give Compound C16 (pyrazole 7' wherein $R^1=NO_2$, $R^2=Cl$, $R^3=CH_2OCH_3$, $R^4=H$) as a red solid.

$^1$H nmr: (DMSO-d6, 300 mHz) 12.27 (s, 1H), 9.11 (s, 1H), 7.86 (dd, J=2, 9 Hz, 1H), 7.43–7.50 (m, 4H), 7.06 (d, J=2 Hz, 1H), 6.72 (d, J=9 Hz, 1H), 4.20 (s, 2H), 3.25 (s, 3H).

H. Methylenation of Aldehyde: $R^3=CHO$ to $R^3=CHCH_2$ 3.16 Compound C17: $R^1=NO_2$, $R^2=Cl$, $R^3=CHCH_2$, $R^4=H$ 3-ethenyl-5-(2-chlorophenyl)-7-nitro-pyrazolo[3,4][1,4]benzodiazepine To a solution of methylene triphenylphosphorane, prepared by reaction of 0.109 g (0.31 mmol) of methyltriphenylphosphonium bromide in 5 mL of tetrahydrofuran and 0.29 mL of 1 M solution of potassium tert.-butoxide in tetrahydrofuran, at −78° C. under an inert atmosphere, was added 0.080 g (0.22 mmol) of pyrazole 7 ($R^1=NO_2$, $R^2=Cl$, $R^3=CHO$, $R^4=H$). The mixture was warmed to reflux, and stirred overnight, after which the mixture was cooled to room temperature, diluted with ethyl acetate and washed successively with water and brine. The ethyl acetate extract was dried over anhydrous sodium sulfate, filtered and concentrated under reduced pressure. Purification by silica gel chromatography, eluting with hexane-ethyl acetate (70/30) gave 0.043 g of Compound C17 (pyrazole 7' wherein $R^1=NO_2$, $R^2=Cl$, $R^3=CHCH_2$, $R^4=H$) as a red solid.

$^1$H nmr: (DMSO-d6, 300 mHz) 12.33 (s, 1H), 9.11 (s, 1H), 7.88 (dd, J=2,9 Hz, 1H), 7.40–7.50 (m, 4H), 7.08 (d, J=2 Hz, 1H), 6.74 (d, J=9 Hz, 1H), 6.40 (dd, J=12, 18 Hz, 1H), 5.85 (d, J=18 Hz, 1H), 5.36 (d, J=12 Hz, 1H).

I. Dehydration of Amide: $R^3=CONH_2$ to $R^3=CN$ 3.17 Compound C18: $R^1=NO_2$, $R^2=Cl$, $R^3=CN$, $R^4=H$ 5-(2-chlorophenyl)-7-nitro-pyrazolo[3,4][1,4]benzodiazepine-3-carbonitrile A mixture of 0.47 g (1.23 mmol) of pyrazole 7 ($R^1=NO_2$, $R^2=Cl$, $R^3=CONH_2$, $R^4=H$), 0.34 g (2.46 mmol) of potassium carbonate, 0.94 g (6.15 mmol) of phosphorous oxychloride and 20 mL of acetonitrile was heated to reflux for 4 hours under an inert atmosphere. The mixture was cooled to room temperature, diluted with ethyl acetate and washed successively with saturated aqueous sodium bicarbonate solution, water and brine, reextracting the aqueous phases with ethyl acetate. The combined ethyl acetate extracts were dried over anhydrous sodium sulfate, filtered and concentrated under reduced pressure. The residue was chromatographed on silica gel eluting with hexane-ethyl acetate (70/30) to give 0.24 g of Compound C18 (pyrazole 7' wherein $R^1=NO_2$, $R^2=Cl$, $R^3=CN$, $R^4=H$) as an orange solid (recrystallization from dichloromethane). mp 193–196° C. IR (KBr) 2240 cm$^{-1}$. $^1$H nmr: (DMSO-d6, 300 mHz) 9.36 (s, 1H), 7.96 (dd, J=2, 9 Hz, 1H), 7.48–7.58 (m, 4H), 7.11 (d, J=2 Hz, 1H), 6.77 (d, J=9 Hz, 1H).

J. Nitrile Hydrolysis $R^1=CN$ to $R^3=CONH_2$.

3.18 Compound C19: $R^1=CONH_2$, $R^2=F$, $R^3=CH_3$, $R^4=H$ 3-methyl-5-(2-fluorophenyl)-pyrazolo[3,4][1,4]benzodiazepine-7-carboxamide To a solution of 0.5 g (1.6 mmol) pyrazole 7 ($R^1=CN$, $R^2=F$, $R^3=CH_3$, $R^4=H$) in 79 mL of dimethylsulfoxide was added 47 mL of ice cold hydrogen peroxide (30% aqueous solution) and 24 mL of 1 M sodium hydroxide. After the reaction was complete, the mixture was extracted with ethyl acetate, and the extracts washed successively with water, brine and then dried over anhydrous sodium sulfate. The mixture was filtered, and concentrated under reduced pressure. Purification by silica gel chromatography (elution with ethyl acetate/methanol (95:5)) gave 0.5 g of Compound C19 (pyrazole 7 wherein $R^1=CONH_2$, $R^2=F$, $R^3=CH_3$, $R^4=H$) as a yellow solid. mp 323–324° C.

$^1$H nmr: (DMSO-d6, 300 mHz) 11.79 (s, 1H), 8.08 (s, 1H), 7.64 (s, 1H), 7.58 (dd, J=2, 9 Hz, 1H), 7.38–7.52 (m, 2H), 7.02–7.30 (m, 4H), 6.73 (d, J=9 Hz, 1H), 2.05 (s, 3H).

Additional compounds not specifically listed in Examples 1-3 above were prepared using the methods described above. These compounds, designated "D," are included in Tables I-IV below.

Example 4

Antiproliferative Activity

The antiproliferative activity of the compounds of the invention is demonstrated below. These effects indicate that the compounds of the present invention are useful in treating cancer, in particular solid tumors such as breast and colon tumors.

CDK2 FlashPlate Assay

To determine inhibition of CDK2 activity, purified recombinant retinoblastoma (Rb) protein was coated on 96 well FlashPlates (New England Nuclear, Boston, Mass.). Rb is a natural substrate for phosphorylation by CDK2 (Herwig and Strauss Eurr. *J. Biochem.*, Vol. 246 (1997) pp. 581–601 and references therein). Recombinant active human Cyclin E/CDK2 complexes were partially purified from extracts of insect cells. The active Cyclin E/CDK2 was added to the Rb-coated Flash Plates along with $^{33}$P-ATP and dilutions of test compounds. Plates were incubated for 25 minutes at room temperature with shaking, then washed and counted in the Topcount scintillation counter (Packard Instrument Co., Downers Grove, Ill.). Dilutions of test compounds were tested in duplicate in each assay. The percent inhibition of Rb phosphorylation, which is a measure of the inhibition of CDK2 activity, was determined according to the following formula:

$$100 \times \left[ 1 - \frac{\text{test compound} - \text{nonspecific}}{\text{total} - \text{nonspecific}} \right]$$

where "test compound" refers to the average counts per minute of the test duplicates, "nonspecific" refers to the average counts per minute when no Cyclin E/CDK2 was added, and "total" refers to the average counts per minute when no compound was added.

The results of the foregoing in vitro experiments are set forth in Tables IA–1C below.

TABLE IA

Inhibition of Cdk2 - IC$_{50}$ Range 0.01–0.99 μM

| Compound Number | R$^1$ (position 7) | R$^2$ (position 2')* | R$^3$ | R$^4$ (position 4') |
|---|---|---|---|---|
| A5 | NO$_2$ | Cl | H | H |
| A13 | NO$_2$ | F | H | H |
| A15 | CN | F | H | H |
| A16 | NO$_2$ | H | H | H |
| A17 | NO$_2$ | CF$_3$ | H | H |
| A20 | CO$_2$Et | F | H | H |
| A21 | H | Cl | H | H |
| B1 | NO$_2$ | Cl | 2-pyrrolyl | H |
| B3 | NO$_2$ | Cl | CH$_3$ | H |
| B4 | NO$_2$ | Cl | CH$_2$CH$_3$ | H |
| B6 | NO$_2$ | Cl | i-Pr | H |
| B7 | CN | F | CH$_3$ | H |
| B9 | CO$_2$Et | F | CH$_3$ | H |
| B10 | NO$_2$ | Cl | 5-(4-Me)-pyrazolyl | H |
| B12 | NO$_2$ | Cl | CF$_3$ | H |
| B13 | NO$_2$ | Cl | 1-thiazolyl | H |
| B14 | NO$_2$ | Cl | 4-imidazolyl | H |
| B15 | NO$_2$ | Cl | 2-pyrazolyl | H |
| B16 | NO$_2$ | Cl | 3-pyrazolyl | H |
| B17 | NO$_2$ | Cl | CH(Me)CH$_2$Me | H |
| B18 | MeO | Cl | CH$_3$ | H |
| B19 | Cl | H | CH$_3$ | H |
| B20 | Cl | Cl | CH$_3$ | H |
| B21 | H | F | CH$_3$ | H |
| B22 | F | H | CH$_3$ | H |
| B23 | NO$_2$ | Cl | Ph | H |
| B24 | NO$_2$ | Cl | propyl | H |
| B25 | NO$_2$ | Cl | cyclopropyl | H |
| B26 | F | F | CH$_3$ | H |
| B27 | NO$_2$ | H | CH$_3$ | H |
| B28 | H | H | CH$_3$ | H |
| B29 | I | F | CH$_3$ | H |
| B30 | H | Cl | CH$_3$ | H |
| B31 | NO$_2$ | F | CH$_3$ | H |
| B32 | Cl | F | CH$_3$ | H |
| B35 | CN | F | CH$_2$OH | H |
| C1 | CON-morpholine amide | F | H | H |
| C2 | CONHCH$_2$CH$_2$OH | F | H | H |
| C4 | NH$_2$ | Cl | CH$_3$ | H |
| C6 | NH$_2$ | Cl | i-Pr | H |
| C7 | AcNH | Cl | CH$_3$ | H |
| C8 | AcryloylNH | Cl | CH$_3$ | H |
| C9 | MsNH | Cl | CH$_3$ | H |
| C10 | NO$_2$ | Cl | CONH$_2$ | H |
| C12 | NO$_2$ | Cl | CONHNH$_2$ | H |
| C13 | NO$_2$ | Cl | CHO | H |
| C14 | NO$_2$ | Cl | CH$_2$OH | H |
| C16 | NO$_2$ | Cl | CH$_2$OMe | H |
| C17 | NO$_2$ | Cl | CH=CH$_2$ | H |
| C18 | NO$_2$ | Cl | CN | H |
| C19 | CONH$_2$ | F | CH$_3$ | H |
| D1 | NO$_2$ | m-NO$_2$** | H | H |
| D2 | NO$_2$ | CF$_3$ | CH$_3$ | H |
| D3 | Me$_2$NSO$_2$NH | Cl | CH$_3$ | H |
| D4 | ClCH$_2$NHSO$_2$NH | Cl | CH$_3$ | H |
| D5 | morpholinylSO$_2$NH | Cl | CH$_3$ | H |
| D6 | NO$_2$ | Cl | 2-thiophenyl | H |
| D7 | NO$_2$ | Cl | 2-furanyl | H |
| D8 | NO$_2$ | Cl | 2-(3-Me)-thiophenyl | H |
| D9 | NO$_2$ | Cl | 3-pyridinyl | H |
| D10 | NO$_2$ | Cl | 4-pyridinyl | H |
| D11 | NO$_2$ | Cl | p-MeSPh | H |
| D12 | NO$_2$ | Cl | p-CF$_3$OPh | H |
| D13 | NO$_2$ | Cl | o,m-methylenedioxy-Ph | H |
| D14 | NO$_2$ | Cl | p-OH-o-MeOPh | H |
| D15 | NO$_2$ | Cl | 3-thiophenyl | H |
| D16 | NO$_2$ | Cl | p-Ph—Ph | H |
| D17 | NO$_2$ | Cl | m-NO$_2$Ph | H |
| D18 | NO$_2$ | H | cyclopropyl | H |
| D50 | CONH$_2$ | F | H | H |
| D51 | CON-morpholine amide | F | CH$_3$ | H |

TABLE IA-continued

Inhibition of Cdk2 - IC$_{50}$ Range 0.01–0.99 μM

| Compound Number | R$^1$ (position 7) | R$^2$ (position 2')* | R$^3$ | R$^4$ (position 4') |
|---|---|---|---|---|
| D52 | CONHCH$_2$CH$_2$OH | F | CH$_3$ | H |
| D53 | CONHCH$_2$CH$_2$—N—morpholinyl | F | CH$_3$ | H |

Unless otherwise indicated.
**Position 3'.

In the remainder of the tables, the position of the substituted R$^1$, R$^2$, R$^3$ and R$^4$ are as provided in Table IA above.

TABLE IB

Inhibition of Cdk2 - IC$_{50}$ Range 1–9.99 μM

| Compound Number | R$^1$ | R$^2$ | R$^3$ | R$^4$ |
|---|---|---|---|---|
| A6 | Cl | H | H | H |
| A7 | Cl | F | H | H |
| A9 | H | H | H | H |
| A10 | H | F | H | H |
| A11 | F | F | H | H |
| A14 | CH$_3$SO$_2$ | H | H | H |
| A18 | CO$_2$CH$_3$ | H | H | H |
| A19 | I | F | H | H |
| B2 | NO$_2$ | Cl | CO$_2$Et | H |
| B5 | NO$_2$ | Cl | CH$_2$CH$_2$Ph | H |
| B8 | NO$_2$ | Cl | CH$_2$Ph | H |
| B11 | NO$_2$ | Cl | CH$_2$-iPr | H |
| B33 | I | H | CH$_3$ | H |
| C3 | CON(CH$_2$CH$_2$OH)$_2$ | F | H | H |
| C5 | NH$_2$ | Cl | H | H |
| C11 | NO$_2$ | Cl | CONMe$_2$ | H |
| D19 | NO$_2$ | Cl | 2-benzofuranyl | H |
| D20 | NO$_2$ | Cl | 2-indoylyl | H |
| D21 | NO$_2$ | Cl | 2-N—Me-pyrrolyl | H |
| D22 | CO$_2$H | F | H | H |
| D23 | NO$_2$ | Cl | m-OH—Ph | H |
| D24 | NO$_2$ | Cl | p-MePh | H |
| D25 | NO$_2$ | Cl | m-CNPh | H |
| D26 | NO$_2$ | Cl | 2-(5-Me)-thiophenyl | H |
| D27 | NO$_2$ | H | 3-pyridinyl | H |
| D28 | NO$_2$ | Cl | p-Me2NPh | H |
| D29 | NO$_2$ | Cl | o-CNPh | H |
| D30 | NO$_2$ | Cl | m-MePh | H |
| D31 | NO$_2$ | Cl | m-EtO-Ph | H |
| D32 | NO$_2$ | Cl | 2-(5-Et)-furanyl | H |
| D33 | NO$_2$ | Cl | 2-naphthyl | H |
| D34 | NO$_2$ | H | 2-imidazolyl | H |
| D35 | CO$_2$Na | H | H | H |
| D37 | NO$_2$ | Cl | o-MePh | H |

TABLE IC

Inhibition of Cdk2 - IC$_{50}$ Range 10–30 μM

| Compound Number | R$^1$ | R$^2$ | R$^3$ | R4 |
|---|---|---|---|---|
| A4 | Cl | Cl | H | H |
| D38 | NO$_2$ | Cl | 1-oxadiazolyl | H |
| D39 | NO$_2$ | Cl | o-NO$_2$Ph | H |
| D40 | NO$_2$ | Cl | o-CF$_3$Ph | H |
| D41 | NO$_2$ | Cl | m-CF$_3$Ph | H |
| D42 | NO$_2$ | Cl | o-MeOPh | H |
| D43 | NO$_2$ | Cl | 4-N-pyrrolylPh | H |
| D44 | NO$_2$ | Cl | m-PhOPh | H |
| D45 | NO$_2$ | H | m,p-methylenedioxy-Ph | H |
| D46 | NO$_2$ | H | m,p-ethylenedioxy-Ph | H |
| D47 | NO$_2$ | H | o-F—Ph | H |

Cell-Based Assays

The estrogen receptor negative epithelial breast carcinoma line (MDA-MB-435) was purchased from American Type Cell Culture Collection (ATCC; Rockville, Md.) and was grown in the medium recommended by ATCC. For analysis of the effect of the test compounds on growth of these cells, the cells were plated at 2000 cells per well in a 96-well tissue culture plate, and were incubated overnight at 37° C. with 5% CO$_2$. The next day, the test compounds were dissolved in 100% dimethyl sulfoxide (DMSO) to yield a 10 mM stock solution. Each compound was diluted with sterile medium to 1 mM in a sufficient quantity to yield a final concentration of 120 μM. The compounds were then serially diluted in medium with 1.2% DMSO. One-fourth final volume of the diluted compounds was transferred to 96 well plates. Test compounds were assayed in duplicate. DMSO was added to a row of "control cells" such that the final concentration of DMSO in each well was 0.3%. Wells to which no cells were added served as the "blank." Wells to which no inhibitor was added served as "no inhibitor control". The plates were returned to the incubator, and 5 days post addition of test compound, were analyzed as described below.

3-(4,5-Dimethylthiazole-2-yl)-2,5-diphenyl-2H-tetrazolium bromide (thiazolyl blue; MTT) was added to each well to yield a final concentration of 1 mg/mL. The plates were then incubated at 37° C. for 3 hours. The plates were centrifuged at 1000 rpm for 5 minutes prior to aspiration of the MTT-containing medium. The MTT-containing medium was then removed and 100 μL 100% ethanol was added to each well to dissolve the resulting formazan metabolite. To ensure complete dissolution, plates were shaken for 15 minutes at room temperature. Absorbencies were read in a microtiter plate reader (Molecular Dynamics) at a wavelength of 570 nm with a 650 nm reference. Percent inhibition was calculated by subtracting the absorbance of the blank (no cell) wells from all wells, then subtracting the division of the average absorbance of each test duplicate by the average of the controls from 1.00. Inhibitory concentrations (IC$_{50}$) were determined from the linear regression of a plot of the logarithm of the concentration versus the percent inhibition.

The results of the foregoing MDA-MB-435 cell-based assay are set forth in Tables IIA–IIC below.

TABLE IIA

Antiproliferative Activity of MDA-MB435 (breast) Assay - IC$_{50}$ Range 0.01–1 μM

| Compound Number | R$^1$ | R$^2$ | R$^3$ | R$^4$ |
|---|---|---|---|---|
| B3 | NO$_2$ | Cl | CH$_3$ | H |
| B4 | NO$_2$ | Cl | CH$_2$CH$_3$ | H |
| B6 | NO$_2$ | Cl | i-Pr | H |
| B7 | CN | F | CH$_3$ | H |

TABLE IIA-continued

Antiproliferative Activity of MDA-MB435 (breast)
Assay - IC$_{50}$ Range 0.01–1 μM

| Compound Number | R$^1$ | R$^2$ | R$^3$ | R$^4$ |
|---|---|---|---|---|
| B22 | F | H | CH$_3$ | H |
| B25 | NO$_2$ | Cl | cyclopropyl | H |
| B29 | NO$_2$ | H | CH$_3$ | H |
| B31 | NO$_2$ | F | CH$_3$ | H |
| B35 | CN | F | CH$_2$OH | H |
| C4 | NH$_2$ | Cl | CH$_3$ | H |
| C7 | AcNH | Cl | CH$_3$ | H |
| C8 | AcryloylNH | Cl | CH$_3$ | H |
| C9 | MsNH | Cl | CH$_3$ | H |
| C13 | NO$_2$ | Cl | CHO | H |
| C14 | NO$_2$ | Cl | CH$_2$OH | H |
| C17 | NO$_2$ | Cl | CH=CH$_2$ | H |
| D3 | Me$_2$NSO$_2$NH | Cl | CH$_3$ | H |

TABLE IIB

Antiproliferative Activity of MDA-MB435 (breast) Assay - IC$_{50}$
Range 1.1–9.99 μM

| Compound Number | R$^1$ | R$^2$ | R$^3$ | R$^4$ |
|---|---|---|---|---|
| A15 | CN | F | H | H |
| B9 | CO$_2$Et | F | CH$_3$ | H |
| B10 | NO$_2$ | Cl | 5-(4-Me)-pyrazolyl | H |
| B12 | NO$_2$ | Cl | CF$_3$ | H |
| B14 | NO$_2$ | Cl | 4-imidazolyl | H |
| B16 | NO$_2$ | Cl | 3-pyrazolyl | H |
| B18 | MeO | Cl | CH$_3$ | H |
| B19 | Cl | H | CH$_3$ | H |
| B20 | Cl | Cl | CH$_3$ | H |
| B21 | H | F | CH$_3$ | H |
| B30 | H | Cl | CH$_3$ | H |
| C6 | NH$_2$ | Cl | i-Pr | H |
| C16 | NO$_2$ | Cl | CH$_2$OMe | H |
| D4 | ClCH$_2$NHSO$_2$NH | Cl | CH$_3$ | H |
| D5 | morpholinylSO$_2$NH | Cl | CH$_3$ | H |
| D51 | CON-morpholine amide | F | CH$_3$ | H |
| D52 | CONHCH$_2$CH$_2$OH | F | CH$_3$ | H |
| D53 | CONHCH$_2$CH$_2$—N—morpholinyl | F | CH$_3$ | H |

TABLE IIC

Antiproliferative Activity of MDA-MB435 (breast)
Assay - IC$_{50}$ Range 10–30 μM

| Compound Number | R$^1$ | R$^2$ | R$^3$ | R$^4$ |
|---|---|---|---|---|
| A5 | NO$_2$ | Cl | H | H |
| A13 | NO$_2$ | F | H | H |
| B2 | NO$_2$ | Cl | CO$_2$Et | H |
| B5 | NO$_2$ | Cl | CH$_2$CH$_2$Ph | H |
| B8 | NO$_2$ | Cl | CH$_2$Ph | H |
| B13 | NO$_2$ | Cl | 1-thiazolyl | H |
| B15 | NO$_2$ | Cl | 2-pyrazolyl | H |
| B24 | NO$_2$ | Cl | Propyl | H |
| C5 | NH$_2$ | Cl | H | H |
| C10 | NO$_2$ | Cl | CONH$_2$ | H |
| C15 | NO$_2$ | Cl | CH$_2$NMe$_2$ | H |
| C18 | NO$_2$ | Cl | CN | H |
| D38 | NO$_2$ | Cl | 1-oxadiazolyl | H |

The colon adenocarcinoma line SW480 and the colon carcinoma line HCT-116 also were obtained from the ATCC and were tested according to the same protocol provided above for MDA-MB-435 cell based assay with the following modifications. Cell line SW480 was plated at 1000 cells per well and analyzed at 6 days post addition of the test compound. Cell line HCT-116 was plated at 1000 cells per well and analyzed at 4 days post addition of test compound.

The results of the foregoing SW480 (colon) and HCT-116 (colon) based assays are set forth below in Tables IIIA–IIIC and IVA–IVC, respectively.

TABLE IIIA

Antiproliferative Activity SW480 (colon) Assay - IC$_{50}$
Range 0.01–1 μM

| Compound Number | R$^1$ | R$^2$ | R$^3$ | R$^4$ |
|---|---|---|---|---|
| B3 | NO$_2$ | Cl | CH$_3$ | H |
| B4 | NO$_2$ | Cl | CH$_2$CH$_3$ | H |
| B6 | NO$_2$ | Cl | i-Pr | H |
| B7 | CN | F | CH$_3$ | H |
| B10 | NO$_2$ | Cl | 5-(4-Me)-pyrazolyl | H |
| B21 | H | F | CH$_3$ | H |
| B26 | F | F | CH$_3$ | H |
| B27 | NO$_2$ | H | CH$_3$ | H |
| B31 | NO$_2$ | F | CH$_3$ | H |
| B35 | CN | F | CH$_2$OH | H |
| C1 | CON-morpholine amide | F | H | H |
| C4 | NH$_2$ | Cl | CH$_3$ | H |
| C7 | AcNH | Cl | CH$_3$ | H |
| C8 | AcryloylNH | Cl | CH$_3$ | H |
| C9 | MsNH | Cl | CH$_3$ | H |
| C14 | NO$_2$ | Cl | CH$_2$OH | H |
| C19 | CONH$_2$ | F | CH$_3$ | H |
| D2 | NO$_2$ | CF$_3$ | CH$_3$ | H |
| D51 | CON-morpholine amide | F | CH$_3$ | H |
| D52 | CONHCH$_2$CH$_2$OH | F | CH$_3$ | H |
| D53 | CONHCH$_2$CH$_2$—N—morpholinyl | F | CH$_3$ | H |

TABLE IIIB

Antiproliferative Activity SW480 (colon)
Assay - IC$_{50}$ Range 1.1–9.99 μM

| Compound Number | R$^1$ | R$^2$ | R$^3$ | R$^4$ |
|---|---|---|---|---|
| A5 | NO$_2$ | Cl | H | H |
| A13 | NO$_2$ | F | H | H |
| A15 | CN | F | H | H |
| B1 | NO$_2$ | Cl | 2-pyrrolyl | H |
| B9 | CO$_2$Et | F | CH$_3$ | H |
| B18 | MeO | Cl | CH$_3$ | H |
| B19 | Cl | H | CH$_3$ | H |
| B20 | Cl | Cl | CH$_3$ | H |
| B22 | F | H | CH$_3$ | H |
| B25 | NO$_2$ | Cl | Cyclopropyl | H |
| B29 | I | F | CH$_3$ | H |
| B30 | H | Cl | CH$_3$ | H |
| B32 | Cl | F | CH$_3$ | H |
| D3 | Me$_2$NSO$_2$NH | Cl | CH$_3$ | H |
| D4 | ClCH$_2$NHSO$_2$NH | Cl | CH$_3$ | H |
| D5 | morpholinylSO$_2$NH | Cl | CH$_3$ | H |
| D50 | CONH$_2$ | F | H | H |

TABLE IIIC

Antiproliferative Activity SW480 (colon)
Assay - IC$_{50}$ Range 10–30 μM

| Compound Number | R$^1$ | R$^2$ | R$^3$ | R$^4$ |
|---|---|---|---|---|
| A9 | H | H | H | H |
| A10 | H | F | H | H |

TABLE IIIC-continued

Antiproliferative Activity SW480 (colon)
Assay - $IC_{50}$ Range 10–30 μM

| Compound Number | $R^1$ | $R^2$ | $R^3$ | $R^4$ |
|---|---|---|---|---|
| A11 | F | F | H | H |
| A21 | H | Cl | H | H |
| B5 | $NO_2$ | Cl | $CH_2CH_2Ph$ | H |
| B8 | $NO_2$ | Cl | $CH_2Ph$ | H |
| B23 | $NO_2$ | Cl | Ph | H |
| B24 | $NO_2$ | Cl | Propyl | H |
| B33 | I | H | $CH_3$ | H |
| C5 | $NH_2$ | Cl | H | H |
| C12 | $NO_2$ | Cl | $CONHNH_2$ | H |
| D6 | $NO_2$ | Cl | 2-thiophenyl | H |
| D7 | $NO_2$ | Cl | 2-furanyl | H |
| D9 | $NO_2$ | Cl | 3-pyridinyl | H |
| D10 | $NO_2$ | Cl | 4-pyridinyl | H |
| D20 | $NO_2$ | Cl | 2-indoylyl | H |
| B34 | Br | H | $CH_3$ | H |
| D36 | $NO_2$-9-$NO_2$ | Cl | H | H |
| D37 | $NO_2$ | Cl | o-MePh | H |
| D40 | $NO_2$ | Cl | o-$CF_3$Ph | H |
| D48 | $NO_2$ | Cl | 1-naphthyl | H |

TABLE IVA

Antiproliferative Activity HCT 116 (colon)
Assay - $IC_{50}$ Range 0.01–1 μM

| Compound Number | $R^1$ | $R^2$ | $R^3$ | $R^4$ |
|---|---|---|---|---|
| B3 | $NO_2$ | Cl | $CH_3$ | H |
| B4 | $NO_2$ | Cl | $CH_2CH_3$ | H |

TABLE IVB

Antiproliferative Activity HCT 116 (colon)
Assay - $IC_{50}$ Range 1.1–9.99 μM

| Compound Number | $R^1$ | $R^2$ | $R^3$ | $R^4$ |
|---|---|---|---|---|
| A15 | CN | F | H | H |
| B1 | $NO_2$ | Cl | 2-pyrrolyl | H |
| B6 | $NO_2$ | Cl | i-Pr | H |
| B7 | CN | F | $CH_3$ | H |
| B9 | $CO_2Et$ | F | $CH_3$ | H |
| B10 | $NO_2$ | Cl | 5-(4-Me)-pyrazolyl | H |
| B25 | $NO_2$ | Cl | Cyclopropyl | H |
| C12 | $NO_2$ | Cl | $CONHNH_2$ | H |
| D50 | $CONH_2$ | F | H | H |

TABLE IVC

Antiproliferative Activity HCT 116 (colon)
Assay - $IC_{50}$ Range 10–30 μM

| Compound Number | $R^1$ | $R^2$ | $R^3$ | $R^4$ |
|---|---|---|---|---|
| A5 | $NO_2$ | Cl | H | H |
| A9 | H | H | H | H |
| A10 | H | F | H | H |
| A13 | $NO_2$ | F | H | H |
| A14 | $CH_3SO_2$ | H | H | H |
| A16 | $NO_2$ | H | H | H |
| A21 | H | Cl | H | H |
| B5 | $NO_2$ | Cl | $CH_2CH_2Ph$ | H |
| B8 | $NO_2$ | Cl | $CH_2Ph$ | H |
| B23 | $NO_2$ | Cl | Ph | H |
| B24 | $NO_2$ | Cl | Propyl | H |

TABLE IVC-continued

Antiproliferative Activity HCT 116 (colon)
Assay - $IC_{50}$ Range 10–30 μM

| Compound Number | $R^1$ | $R^2$ | $R^3$ | $R^4$ |
|---|---|---|---|---|
| C1 | CON-morpholine amide | F | H | H |
| C2 | $CONHCH_2CH_2OH$ | F | H | H |
| C5 | $NH_2$ | Cl | H | H |
| D6 | $NO_2$ | Cl | 2-thiophenyl | H |
| D7 | $NO_2$ | Cl | 2-furanyl | H |
| D8 | $NO_2$ | Cl | 2-(3-Me)-thiophenyl | H |
| D9 | $NO_2$ | Cl | 3-pyridinyl | H |
| D10 | $NO_2$ | Cl | 4-pyridinyl | H |
| D11 | $NO_2$ | Cl | p-MeSPh | H |
| D12 | $NO_2$ | Cl | p-$CF_3$OPh | H |
| D13 | $NO_2$ | Cl | o,m-methylenedioxy-Ph | H |
| D14 | $NO_2$ | Cl | p-OH-o-MeOPh | H |
| D18 | $NO_2$ | H | cyclopropyl | H |
| D19 | $NO_2$ | Cl | 2-benzofuranyl | H |
| D20 | $NO_2$ | Cl | 2-indoylyl | H |
| D36 | $NO_2$-9-$NO_2$ | Cl | H | H |
| D37 | $NO_2$ | Cl | o-MePh | H |
| D41 | $NO_2$ | Cl | m-$CF_3$Ph | H |
| D43 | $NO_2$ | Cl | 4-N-pyrrolylPh | H |
| D48 | $NO_2$ | Cl | 1-naphthyl | H |
| D49 | $NO_2$ | Cl | 4-isoquinolinyl | H |

| | Ingredients | Mg/Tablet | | | | | |
|---|---|---|---|---|---|---|---|
| H | | | | | | | |
| I | Compound 1* | 5 | 25 | 100 | 250 | 500 | 750 |
| J | Anhydrous Lactose | 103 | 83 | 35 | 19 | 38 | 57 |
| K | Croscarmellose Sodium | 6 | 6 | 8 | 16 | 32 | 48 |
| L | Povidone K30 | 5 | 5 | 6 | 12 | 24 | 36 |
| M | Magnesium Stearate | 1 | 1 | 1 | 3 | 6 | 9 |
| N | Total Weight | 120 | 120 | 150 | 300 | 600 | 900 |

*Compound 1 represents a compound of the invention.

Manufacturing Procedure:

1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 6

Capsule Formulation

| | Ingredients | mg/Capsule | | | | |
|---|---|---|---|---|---|---|
| O | | | | | | |
| P | Compound 1* | 5 | 25 | 100 | 250 | 500 |
| Q | Anhydrous Lactose | 159 | 123 | 148 | — | — |
| R | Corn Starch | 25 | 35 | 40 | 35 | 70 |
| S | Talc | 10 | 15 | 10 | 12 | 24 |
| T | Magnesium Stearate | 1 | 2 | 2 | 3 | 6 |
| U | Total Fill Weight | 200 | 200 | 300 | 300 | 600 |

*Compound 1 represents a compound of the invention.

Manufacturing Procedure:

1. Mix Items 1, 2 and 3 in a suitable mixer for 15 minutes.
2. Add Items 4 & 5 and mix for 3 minutes.
3. Fill into a suitable capsule.

Example 7

Injection Solution/Emulsion Preparation

| Item | Ingredient | mg/mL |
|------|------------|-------|
| 1 | Compound 1* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound 1 represents a compound of the invention.

Manufacturing Procedure:

1. Dissolve item 1 in item 2.
2. dd items 3, 4 and 5 to item 6 and mix until dispersed, then homogenize.
3. Add the solution from step 1 to the mixture from step 2 and homogenize until the dispersion is translucent.
4. terile filter through a 0.2 um filter and fill into vials.

Example 8

Injection Solution/Emulsion Preparation

| Item | Ingredient | mg/mL |
|------|------------|-------|
| 1 | Compound 1* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound 1 represents a compound of the invention.

Manufacturing Procedure:

1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 um filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:
1. A compound of formula

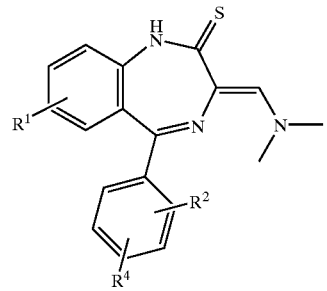

wherein:
$R^1$ is selected from the group consisting of
—H,
—$NO_2$,
—CN,
-halogen,
-lower alkyl which is straight-chained and which optionally may be substituted by the group consisting of —OH and halogen,
—$OR^5$,
—$R^6$—$OR^7$,
—$COOR^7$,
—$CONR^8R^9$,
—$NR^{10}R^{11}$,
—$NHCOR^{12}$, and
—$NHSO_2R^{13}$;
$R^2$ and $R^4$ are each independently selected from the group consisting of
—H,
-halogen,
—$NO_2$,
—$CF_3$, and
—straight chained lower alkyl;
$R^5$ is selected from lower alkyl which optionally may be substituted by halogen;
$R^6$ is selected from —$(CH_2)_{1-6}$—;
$R^7$ is selected from the group consisting of —H and lower alkyl;
$R^8$ and $R^9$ are each independently selected from the group consisting of —H and -lower alkyl which itself optionally may be substituted by —OH and —$NH_2$; alternatively, $R^8$ and $R^9$ may form a 5- or 6-membered heterocycle which optionally may be substituted by the group consisting of —OH, —$NH_2$, and lower alkyl;
$R^{10}$, $R^{11}$ and $R^{12}$ are each independently selected from the group consisting of —H and lower alkyl;
$R^{13}$ is selected from the group consisting of lower alkyl which optionally may be substituted by the group consisting of halogen and —$NR^{14}R^{15}$; and
$R^{14}$ and $R^{15}$ are each independently selected from the group consisting of —H and lower alkyl which optionally may be substituted halogen, or alternatively, —$NR^{14}R^{15}$ is a heterocycle.

2. The compound of claim 1, wherein $R^1$ is on position 7 and is selected from the group consisting of —H, —$NO_2$, —CN, halogen and lower alkyl.

3. The compound of claim 1, wherein $R^1$ is on position 8 and is selected from the group consisting of —H, —$NO_2$, —CN, halogen and lower alkyl.

4. A compound of formula

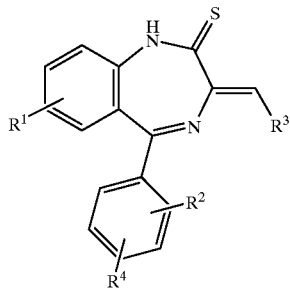

wherein:
R$^1$ is selected from the group consisting of
- —H,
- —NO$_2$,
- —CN,
- -halogen,
- -lower alkyl which is straight-chained and which optionally may be substituted by the group consisting of —OH and halogen,
- —OR$^5$,
- —R$^6$—OR$^7$,
- —COOR$^7$,
- —CONR$^8$R$^9$,
- —NR$^{10}$R$^{11}$,
- —NHCOR$^{12}$, and
- —NHSO$_2$R$^{13}$;

R$^2$ and R$^4$ are each independently selected from the group consisting of
- —H,
- -halogen,
- —NO$_2$,
- —CF$_3$, and
- -straight chained lower alkyl;

R$^3$ is selected from the group consisting of
- —H,
- -lower alkyl which optionally may be substituted by —OH,
- —OR$^9$, F, and aryl,
- -cycloalkyl,
- -aryl,
- -heterocycle,
- -heteroaryl,
- —COOR$^7$
- —CN,
- -alkenyl,
- —CONR$^8$R$^9$, and
- -alkynyl;

R$^5$ is selected from lower alkyl which optionally may be substituted by halogen;
R$^6$ is selected from —(CH$_2$)$_{1-6}$—;
R$^7$ is selected from the group consisting of —H and lower alkyl;
R$^8$ and R$^9$ are each independently selected from the group consisting of —H and —lower alkyl which itself optionally may be substituted by —OH and —NH$_2$; alternatively, R$^8$ and R$^9$ may form a 5- or 6-membered heterocycle which optionally may be substituted by the group consisting of —OH, —NH$_2$, and lower alkyl;
R$^{10}$, R$^{11}$ and R$^{12}$ are each independently selected from the group consisting of —H and lower alkyl;

R$^{13}$ is selected from the group consisting of lower alkyl which optionally may be substituted by the group consisting of halogen and —NR$^{14}$R$^{15}$; and
R$^{14}$ and R$^{15}$ are each independently selected from the group consisting of —H and lower alkyl which optionally may be substituted halogen, or alternatively, —NR$^{14}$R$^{15}$ is a heterocycle.

5. The compound of claim 4 wherein R$^1$ is on position 7 and is selected from the group consisting of —H, —NO$_2$, —CN, halogen and lower alkyl.

6. The compound of claim 4, wherein R$^1$ is on position 8 and is selected from the group consisting of —H, —NO$_2$, —CN, halogen and lower alkyl.

7. The compound of claim 5 wherein R$^1$ is methyl or ethyl.

8. The compound of claim 6 wherein R$^1$ is methyl or ethyl.

9. The compound of claim 1, wherein R$^2$ is on the 2' position and is selected from the group consisting of H and halogen.

10. The compound of claim 4 wherein R$^3$ is selected from the group consisting of lower alkyl, cycloalkyl, heterocycle, and heteroaryl.

11. The compound of claim 10 wherein R$^3$ is selected from the group consisting of methyl and ethyl.

12. The compound of claim 10 wherein R$^3$ is C$_3$–C$_5$ cycloalkyl.

13. The compound of claim 4 wherein R$^4$ is at the 4' position and is selected from the group consisting of H and halogen.

14. The compound of claim 4 wherein R$^5$ is selected from the group consisting of methyl and ethyl, each of which optionally may be substituted by halogen.

15. The compound of claim 14 wherein R$^5$ is trifluoromethyl.

16. The compound of claim 4 wherein R$^7$ is selected from the group consisting of —H, methyl and ethyl.

17. The compound of claim 4 wherein R$^8$ is selected from the group consisting of H, methyl, ethyl, and hydroxyethyl.

18. The compound of claim 4 wherein R$^9$ is selected from the group consisting of H, methyl, ethyl, and hydroxyethyl.

19. The compound of claim 4 wherein R$^8$ and R$^9$ form a heterocycle.

20. The compound of claim 19 wherein R$^8$ and R$^9$ form a 6-membered heterocycle that includes two heteroatoms.

21. The compound of claim 20 wherein the heteroatoms are independently selected from O and N.

22. The compound of claim 4 wherein R$^{10}$, R$^{11}$ and R$^{12}$ are each independently selected from the group consisting of —H, methyl and ethyl.

23. The compound of claim 4 wherein R$^{13}$ is lower alkyl which optionally may be substituted by halogen.

24. The compound of claim 23 wherein R$^{13}$ is selected from the group consisting of methyl, ethyl and trifluoromethyl.

25. The compound of claim 4 wherein R$^{14}$ and R$^{15}$ are each independently selected from the group consisting of H, methyl, and ethyl, or alternatively, the group NR$^{14}$R$^{15}$ is a heterocycle.

26. The compound of claim 25 wherein the heterocycle is a 3–7 membered ring that includes at least one nitrogen atom.

* * * * *